US011904077B2

(12) United States Patent
Schlienger et al.

(10) Patent No.: US 11,904,077 B2
(45) Date of Patent: Feb. 20, 2024

(54) BREASTPUMP

(71) Applicant: MEDELA HOLDING AG, Baar (CH)

(72) Inventors: André Schlienger, Maschwanden (CH); Sebastian Höner, Thalwil (CH); Mario Rigert, Buchrain (CH); Armin Felber, Lucerne (CH); Marco Steiner, Cham (CH)

(73) Assignee: MEDELA HOLDING AG, Baar (CH)

( * ) Notice: Subject to any disclaimer, the term of this patent is extended or adjusted under 35 U.S.C. 154(b) by 469 days.

(21) Appl. No.: 16/756,092

(22) PCT Filed: Oct. 24, 2017

(86) PCT No.: PCT/EP2017/077141
§ 371 (c)(1),
(2) Date: Apr. 14, 2020

(87) PCT Pub. No.: WO2019/080995
PCT Pub. Date: May 2, 2019

(65) Prior Publication Data
US 2021/0121614 A1  Apr. 29, 2021

(51) Int. Cl.
*A61M 1/06* (2006.01)
*A61M 39/24* (2006.01)

(52) U.S. Cl.
CPC .............. *A61M 1/06* (2013.01); *A61M 1/064* (2014.02); *A61M 1/0697* (2021.05); *A61M 39/24* (2013.01)

(58) Field of Classification Search
CPC .......... A61M 1/06; A61M 1/80; A61M 39/24; A61M 1/064; A61M 1/0697; A61M 1/067; A61M 1/066; A61M 2210/1007; A61M 1/82; A61M 1/0693; A61M 1/062
See application file for complete search history.

(56) References Cited

U.S. PATENT DOCUMENTS

| | | | |
|---|---|---|---|
| 2008/0255503 A1* | 10/2008 | Quackenbush | A61M 1/74 604/74 |
| 2009/0254029 A1 | 10/2009 | Tashiro et al. | |
| 2010/0121265 A1 | 5/2010 | Bryan et al. | |

(Continued)

FOREIGN PATENT DOCUMENTS

| | | |
|---|---|---|
| CN | 101549180 A | 10/2009 |
| CN | 102271726 A | 12/2011 |

(Continued)

OTHER PUBLICATIONS

International Search Report for International Application No. PCT/EP2017/077141, dated Sep. 20, 2018.

(Continued)

*Primary Examiner* — Brandy S Lee
*Assistant Examiner* — Robert F Allen
(74) *Attorney, Agent, or Firm* — MARSHALL, GERSTEIN & BORUN LLP

(57) ABSTRACT

A breastpump for expressing human breastmilk includes a multipart hygiene module having a first part with a flow opening for connecting to a interior, a valve body with at least one valve and a second part with a rigid cup for forming a pump chamber. The valve body is arranged between the first and second part and the hygiene module as a whole is connectable to the housing of the breastpump in a sealing and detachable manner.

46 Claims, 25 Drawing Sheets

(56) References Cited

U.S. PATENT DOCUMENTS

| | | | |
|---|---|---|---|
| 2010/0121266 A1 | 5/2010 | Bryan et al. | |
| 2011/0098639 A1 | 4/2011 | Kirchner | |
| 2012/0070323 A1 | 3/2012 | Felber et al. | |
| 2012/0071820 A1 | 3/2012 | Luzbetak et al. | |
| 2012/0277728 A1* | 11/2012 | Weber | A61M 1/0697 604/74 |
| 2012/0316493 A1 | 12/2012 | Schlienger et al. | |
| 2013/0053764 A1* | 2/2013 | Jaeger-Waldau | A61M 1/06 604/74 |
| 2016/0000982 A1* | 1/2016 | Alvarez | A61M 1/064 604/74 |
| 2018/0093024 A1* | 4/2018 | Analytis | A61M 1/062 |
| 2018/0333523 A1* | 11/2018 | Chang | A61M 1/06 |

FOREIGN PATENT DOCUMENTS

| | | |
|---|---|---|
| CN | 102596280 A | 7/2012 |
| CN | 103118718 A | 5/2013 |
| EP | 3058967 A1 | 8/2016 |
| RU | 2337717 C1 | 11/2008 |
| TW | 200714305 A | 4/2007 |
| WO | WO-2011/035447 A1 | 3/2011 |
| WO | WO-2013/049944 A1 | 4/2013 |
| WO | WO-2016/014469 A1 | 1/2016 |
| WO | WO-2016/014494 A1 | 1/2016 |
| WO | WO-2016/131677 A1 | 8/2016 |
| WO | WO-2017/144282 A1 | 8/2017 |

OTHER PUBLICATIONS

Office Action for Russian Application No. 2020115691, dated Jan. 15, 2021.

Office Action for TW Application No. 11120819200 dated Aug. 22, 2022.

The Second Office Action for Chinese Application 201780096228.7, dated Nov. 28, 2022.

* cited by examiner

BREASTPUMP

CROSS-REFERENCE TO RELATED APPLICATION

This present application is the US national phase of International Patent Application No. PCT/EP2017/077141, filed Oct. 24, 2017. The priority application is hereby incorporated by reference in its entirety.

TECHNICAL FIELD

The present invention relates to a breastpump for expressing human breastmilk and a breast shield, a milk collection container and a method for operating a breastpump.

PRIOR ART

Devices for expressing human breastmilk are sufficiently well known. In principle, there are two different types: the first type is operated manually, i.e., the negative pressure necessary for expressing is produced by manual actuation of the vacuum pump. In the second type, the vacuum pump is operated electrically.

These vacuum pumps are connected to a breast shield, either directly or by way of a vacuum line. The breast shield comprises an interior for receiving the mother's breast or the nipple thereof. The negative pressure is transferred into the interior via a first line; the expressed milk flows into a milk collection container via a second line.

WO 2016/014494 A1 and WO 2016/014469 A1 describe a compact breastpump, in which expressed milk is transported to a milk collection container under positive pressure. To this end, a milk line is cyclically squeezed, for example.

WO 2011/035447 A1 discloses a breastpump in which the vacuum line forms the milk line at the same time. The pump chamber, in which the negative pressure is produced, fills with milk during expressing such that the pump system changes from a pneumatic system to a hydraulic system and the already expressed milk becomes the working fluid. A valve is arranged at the output of the pump chamber, which leads to the milk collection container, so that the pump chamber can be filled with milk. This valve only opens at a certain pressure within the pump chamber, i.e., once the pump chamber has been sufficiently filled with milk.

This combined pneumatic and hydraulic pump has a number of advantages. The system has no dead volume or almost no dead volume. The pump unit can be minimized since, after the system has been filled with milk, only little pump power is still required to express further milk. In particular, it is possible to use batteries with a lower capacity than in the case of pneumatic vacuum pumps. Consequently, the vacuum pump can be embodied in a more cost-effective and smaller manner. The breastpump is particularly suitable for so-called "hands-free" applications, in which the breastpump is carried on the body and no hands are required for securing the breast shield. Moreover, the applied pressure can be controlled more easily on account of the minimized dead volume. As a result, it is possible to choose pump parameters that are individually optimized to each mother.

WO 2013/049944 A2 likewise describes a breastpump which changes from a pneumatic pump system into a hydraulic pump system. A pressure sensor, which comprises a vane attached to a flexible membrane, is present in the pump chamber.

SUMMARY OF THE INVENTION

Thus, it is an object of the invention to optimize the aforementioned breastpump.

In a preferred embodiment, the breastpump according to the invention for expressing human breastmilk comprises a housing with a drive unit, a pump chamber with a flexible pump membrane, driven by the drive unit, for producing a vacuum, and a breast shield with an interior for receiving breastmilk. A cyclically changing negative pressure is appliable to the interior by means of the pump chamber, wherein a milk channel leads from the interior into the pump chamber through a first inlet opening, wherein expressed milk flows from the interior of the breast shield into the pump chamber through the milk channel and wherein the pump chamber has an outlet opening, through which the expressed milk flows from the pump chamber into a milk collection container. A multipart hygiene module is present, wherein the hygiene module comprises a first part with a flow opening for connecting to the interior, a valve body with at least one valve and a second part with a rigid cup for forming the pump chamber, wherein the valve body is arranged between the first and second part and wherein the hygiene module as a whole is connectable to the housing of the breastpump in a sealing and detachable manner.

This hygiene module has a compact design. It can be easily assembled and taken apart, and so the relevant parts of the breastpump can be easily cleaned. The use of a valve body in the hygiene module additionally simplifies the production, the assembly and the cleaning.

Preferably, the rigid cup has a milk path which leads from the pump chamber into a milk collection container and which, at least over a portion, extends perpendicular to a drive axis of the pump membrane. Preferably, the milk path extends in a plane perpendicular to the drive axis, wherein the milk path extends over at least half of the height of the pump chamber, preferably over the entire height of the pump chamber, in this plane. The extent of this milk path renders it possible to fill the pump chamber with expressed milk, at least in part, preferably in full, such that, during the expressing process, a change is carried out from a pneumatic pump system to a mixed pump system or even to a pump system operating completely on hydraulic principles.

Preferably, the valve body comprises at least one flow valve and one venting valve. Preferably, the valve body is formed in integral fashion from a flexible material. This makes both production, and assembly and cleaning easier.

Preferably, the first part is a constituent part of the breast shield. As a result, the breastpump can have a compact embodiment and the hygiene module can be fastened in a simple manner to the breastpump, without the breast shield still needing to be additionally assembled.

Preferably, the breast shield has a flange for detachably connecting to the housing.

The connection to the housing can be established in a particularly simple manner if it is interlocking and a force fit, preferably a bayonet lock.

In a further preferred embodiment, the breastpump according to the invention for expressing human breastmilk comprises a breast shield with an interior for receiving a mother's breast and a pump chamber, wherein a cyclically changing negative pressure is appliable to the interior by means of the pump chamber. A milk channel leads from the interior into the pump chamber through a first inlet opening, expressed milk flowing through said milk channel from the interior of the breast shield into the pump chamber. The pump chamber has an outlet opening, through which the expressed milk flows from the pump chamber into a milk collection container. The outlet opening, at least at the start of an expressing process, is arranged in an upper region of the pump chamber and/or above the inlet opening in the vertical use position of the breastpump.

As a result, the pump chamber can be nearly completely filled with milk and the system can be converted within a very short time from a pneumatic into a hydraulic or mixed pneumatic/hydraulic system. The same drive power for the pump means, e.g., the pump membrane, leads to a greater pump capacity, i.e., to a greater negative pressure in terms of absolute value in the pump chamber and hence in the interior of the breast shield. It is possible to use batteries with a lower capacity. This reduces production costs, increases the service life of the pump overall and minimizes the size of the drive unit.

Preferably, the milk channel forms a vacuum channel for applying the cyclically changing negative pressure to the interior of the breast shield. That is to say, the vacuum is applied first and the milk is subsequently sucked away via the same line or same channel. The same line or same channel is used for both working fluids, i.e., air and milk.

Depending on the embodiment, the pump is a reciprocating pump, a diaphragm pump or any other type of vacuum pump. Preferably, however, the pump chamber comprises a rigid first cup and a flexible pump membrane, wherein the pump membrane rests against the first cup in sealing fashion and wherein the pump membrane is driven and a negative pressure is producible in the pump chamber as a result of the movement of said pump membrane relative to the first cup.

Preferably, a flexible media separation membrane is arranged between the rigid cup and the flexible pump membrane such that the pump membrane is protected from contact with expressed milk. Milk and air, which are present in the breast shield, only reach up to the media separation membrane. Consequently, the pump membrane and the remaining parts of the breastpump are protected from contamination.

The media separation membrane can be easily separated from the pump membrane. It is preferably part of the hygiene module already mentioned. The media separation membrane can preferably be separated from the remaining parts of the hygiene module and thus be easily cleaned. The remaining parts of the hygiene module, too, can be separated from one another to the extent that this is necessary, and so these can be cleaned and subsequently reassembled in a simple manner and preferably without tools, and can be used again.

Preferably, the first cup has an outlet groove, which extends from the outlet opening of the pump chamber to an output, wherein the outlet groove, at least over a portion, extends in a direction perpendicular to the movement direction of the pump membrane. Preferably, it extends in a plane perpendicular to this movement direction, wherein the groove extends preferably over at least half of the height of the pump chamber, preferably over the entire pump chamber.

In other embodiments, the groove is partly or completely embodied as a closed channel. However, preferably, the pump membrane or, if present, the media separation membrane closes off the outlet groove of the rigid first cup to form a channel that is closed apart from the outlet opening and the output.

Preferably, the groove extends next to the pump chamber and not within same.

In a preferred embodiment, the breast shield has a first passage opening, which forms part of the milk channel, wherein the passage opening, at least at the start of the expressing process, is arranged in an upper region of the interior in the use position of the breast shield such that the interior below the first passage opening is fillable with expressed milk.

As a result, the breast shield can be partly or completely filled with milk at the start of the expressing process. This once again massively reduces the time until the change to the hydraulic pump system. Usually, the interior of the breast shield is filled first, followed by the pump chamber, before the milk reaches the milk collection container for the first time.

Preferably, the milk channel is able to be closed off by means of a first valve in order to remove the expressed milk from the pump chamber at the end of the expressing process. This valve is preferably the same valve that independently opens and closes when the milk is being expressed. Now, it is permanently closed for draining purposes. Depending on the embodiment, closing off is implemented manually or automatically, e.g., by means of the electronic controller of the breastpump. If a valve is disposed downstream, the first valve also can be always open during the expressing process.

Preferably, a draining channel is present between the interior of the breast shield and the pump chamber, said draining channel extending separately from the milk channel, wherein the draining channel is able to be closed off by means of a second valve. The draining channel is closed during the expressing process and opened at the end of the expressing process. Depending on the embodiment, this is also implemented manually or automatically. The second valve preferably operates on the same or similar principles as the first valve. It preferably has an identical embodiment. It opens and closes during the pumping process when the breast shield is drained in the same way as the first valve during the expressing of the breastmilk from the mother's breast. If a valve is disposed downstream, the second valve also can be always open during the draining process.

Preferably, a venting valve for venting the interior of the breast shield is moreover present. Said venting valve is likewise preferably always closed during the expressing process and opened manually or automatically to simplify draining of the breast shield.

Preferably, the venting valve is able to be closed off together with the second valve and said venting valve can be opened together with the latter.

In a preferred embodiment, a third valve is present, said third valve maintaining a baseline negative pressure in the interior of the breast shield when the pressure of the cyclically changing negative pressure increases. Consequently, the pressure in the interior of the breast shield lies below atmospheric pressure during the entire expressing process and, preferably, during draining, too. This reduces the load on the nipple and has a positive influence on the milk flow from the mother's breast.

Preferably, a fourth valve is present in the milk channel, said fourth valve opening and closing in accordance with the applied negative pressure. This fourth valve is arranged following the first valve in the expressing direction of the milk. However, as already described above, the fourth valve also can be formed by the first valve. However, if it is disposed downstream, it can be embodied as a flutter valve in the valve body, for example.

Preferably, a fifth valve is present in the draining channel, said fifth valve opening and closing in accordance with the applied negative pressure. This fifth valve is arranged following the second valve in the draining direction of the milk. However, as already described above, the fifth valve also can be formed by the second valve. If it is disposed downstream, it can be embodied as a flutter valve in the valve body, for example.

Preferably, at least some, preferably all, of the aforementioned valves are arranged in a common valve body. This simplifies the production and minimizes the costs.

Preferably, the valve body has an integral and flexible embodiment. Preferably, it consists of silicone.

Preferably, the breastpump comprises a pump housing with a drive for the pump membrane, wherein the rigid first cup is detachably connected to the pump housing. This simplifies the assembly, also after cleaning by the mother.

Preferably, the first rigid cup is a constituent part of a multipart module, which is connectable together to the pump housing, wherein the module moreover at least comprises the aforementioned valves. This module preferably is the aforementioned hygiene module.

Preferably, the first rigid cup is a constituent part of an adapter part, wherein the valve body is held in a receptacle of the adapter part. This simplifies the assembly and, in particular, facilitates a modular design and the use of a hygiene module.

Preferably, the module further comprises a manual actuation means for simultaneous actuation of the first and second valve. Manual actuation of the two valves is a cost-effective and reliable solution.

Preferably, the adapter part and the actuation part are not detachable from one another in a non-destructive manner. This ensures that the module is always correctly assembled and can only be used with all elements together.

Preferably, the breastpump comprises a pump housing, wherein the breast shield is fastenable to the pump housing in a detachable manner and wherein, as a result of fastening the breast shield to the pump housing, parts that lie between the breast shield and the pump housing are connected to one another in sealing fashion such that a tight connection arises between the pump chamber and the interior of the breast shield. The breast shield can be easily held in the hand, simplifying the assembly of the pump. Since the remaining parts likewise rest in sealing fashion at the pump housing as a result of fastening the breast shield, the breastpump is consequently ready to use with a single movement of the hand, namely that for fastening the breast shield to the pump housing. The individual parts can be removed just as easily in order to be cleaned. Preferably, the breast shield and the valve body are parts of the module.

Preferably, the breastpump comprises a pump housing, to which the breast shield is fastenable in a detachable manner, wherein the breastpump further comprises a milk collection container, which is fastenable to the pump housing by means of a snap-fit connector. The use of a snap-fit connector for fastening the milk collection container is unconventional. Screw caps are usually used. Thanks to the snap-fit connector, the container can have a different embodiment and, in particular, can be fastened and removed more quickly.

Preferably, the milk collection container comprises a main body and a lid, wherein the lid has an at least partly air-permeable and liquid-impermeable embodiment. Consequently, this lid forms a valve serving for ventilation but also allowing the container to be placed on its head without liquid being lost. Preferably, the lid comprises an air-permeable and liquid-impermeable membrane. Preferably, the lid is clamped between the milk collection container and the pump and positionable by means of spacer pins.

Moreover, the lid is preferably provided with a one-way valve, which leads from the pump chamber into the milk collection container.

In a preferred embodiment, the breastpump for expressing human breastmilk comprises a breast shield with an interior for receiving a mother's breast and a pump chamber, wherein a cyclically changing negative pressure is appliable to the interior by means of the pump chamber. A milk channel leads from the interior into the pump chamber through a first inlet opening, expressed milk flowing through said milk channel from the interior of the breast shield into the pump chamber. The pump chamber has an outlet opening, through which the expressed milk flows from the pump chamber into a milk collection container. A draining channel is present between the interior of the breast shield and the pump chamber, said draining channel extending separately from the milk channel, wherein the draining channel is able to be closed by means of a valve, wherein the draining channel is closed during the expressing process and opened at the end of the expressing process. As a result, milk can easily be removed from the breast shield at the end of the expressing process. Preferably, negative pressure is applied to the draining channel by means of the pump chamber in order to actively express milk and push it into the milk collection container.

In a preferred embodiment, the breastpump for expressing human breastmilk comprises a breast shield with an interior for receiving a mother's breast and a pump chamber, wherein a cyclically changing negative pressure is appliable to the interior by means of the pump chamber. A milk channel leads from the interior into the pump chamber through a first inlet opening, expressed milk flowing through said milk channel from the interior of the breast shield into the pump chamber. The pump chamber has an outlet opening, through which the expressed milk flows from the pump chamber into a milk collection container. The breastpump comprises a pump housing, a pump membrane and a module, wherein the module comprises at least a rigid cup for forming the pump chamber and the breast shield. The module is fastenable to the pump housing as a unit, wherein a sealed connection is created between the pump chamber and the interior of the breast shield and wherein the pump membrane is kept in sealing fashion between the module and the pump housing. This simplifies cleaning of the relevant parts of the breastpump by the mother and the reassembly after such cleaning.

Preferably, the module further comprises a valve body, which is arranged between the breast shield and rigid cup. The valve body and the corresponding regions of the first and second part, which preferably have sealing seats for the valves of the valve body, form a common valve unit, which is also referred to as a valve construct.

Preferably, the module further comprises a manual actuation means for actuating at least one valve of the valve construct.

In a preferred embodiment, the breastpump for expressing human breastmilk comprises a breast shield for receiving a mother's breast, a pump housing and a milk collection container, wherein the pump housing is firstly detachably connectable to the breast shield and secondly detachably connectable to the milk collection container. The milk collection container is fastenable to the pump housing by means of a snap-fit connector.

Preferably, this breastpump comprises a pump chamber and a milk channel, through which expressed milk flows from an interior of the breast shield into the pump chamber, wherein the pump chamber has an output, which is connected to the milk collection container and through which the expressed milk flows into the milk collection container.

In a preferred embodiment, there is a milk collection container according to the invention for connecting to a pump housing of a breastpump for expressing human breastmilk, wherein the milk collection container comprises a lid, which faces the pump housing and which, at least in one region, is air permeable and liquid impermeable.

In a preferred embodiment, the breastpump for expressing human breastmilk comprises a breast shield for receiving a mother's breast and a pump housing, wherein the breast shield is detachably connectable to the pump housing. The breast shield is connectable to the pump housing by means of a bayonet lock.

In a preferred embodiment, a breast shield according to the invention is present, said breast shield serving for fastening to a pump housing of a breastpump. The breast shield comprises an interior for receiving the mother's breast and a connector for attaching to the pump housing, wherein the connector is provided with a bayonet lock.

In a preferred variant of a method according to the invention for actuating a breastpump for expressing human breastmilk, the breastpump comprises a breast shield with an interior for receiving a mother's breast and a pump chamber, wherein a cyclically changing negative pressure is applied to the interior by means of the pump chamber. In a first pump phase, the cyclically changing negative pressure is applied to the interior in order to express milk from the mother's breast, wherein the interior is filled with expressed milk without expressed milk flowing out of the interior. In a second pump phase, expressed milk flows from the interior into the pump chamber and the pump chamber is filled with expressed milk. In a third pump phase, the expressed milk flows from the pump chamber into a milk collection container, with the interior and the pump chamber remaining filled with expressed milk. The change from the second pump phase to the third pump phase is implemented by virtue of a fill level of the expressed milk reaching an outlet opening, which leads from the pump chamber to the milk collection container, as a result of which milk flows from the pump chamber into the milk collection container through the outlet opening.

Thanks to this method, the pump system converts relatively quickly from a pneumatic to a hydraulic or predominantly hydraulic pump system. As a result of this, it is possible to use smaller drives and less powerful motors.

Preferably the first pump phase is a completely or predominantly pneumatic pump phase and the second pump phase is a completely or predominantly hydraulic pump phase.

In a preferred variant of the method, the interior is nearly completely filled during the first pump phase. In a preferred variant, the interior and/or the pump chamber are nearly completely filled with expressed milk during the second and/or third pump phase.

Preferably, the change from the first pump phase to the second pump phase is implemented by virtue of a fill level of the expressed milk reaching a first passage opening, which leads from the interior to the pump chamber, as a result of which milk flows from the interior into the pump chamber through the first passage opening.

Preferably, in the third pump phase, the expressed milk flows through the first passage opening into the pump chamber and flows through the outlet opening into the milk collection container.

Preferably, in a fourth pump phase, the interior is drained and the already expressed milk contained therein is guided from the interior to the milk collection container through a second passage opening.

Preferably, the first passage opening is able to be closed off with a first valve and the second passage opening is able to be closed off with a second valve, wherein the second passage opening always remains closed during the first to third pump phase.

Preferably, the first passage opening is always closed during the fourth pump phase.

Preferably, the second passage opening leads from the interior into the pump chamber and has a fluid-communicating connection to the outlet opening via the pump chamber.

Preferably, a baseline negative pressure is maintained during at least some of the pump phases, preferably during the first, second and third pump phase.

Preferably, a third valve is present, said third valve initially opening in the case of a pressure increase of the cyclically changing negative pressure in the direction of atmospheric pressure and then closing and thereby maintaining the baseline negative pressure.

Further embodiments and variants of the method are specified in the dependent claims.

The individual elements cited in the claims can also be assembled in other combinations, without all features of the claims having to be adopted. In particular, individual elements can also be used in purely pneumatic breastpumps, in particular in pneumatic membrane breastpumps.

BRIEF DESCRIPTION OF THE DRAWINGS

Preferred embodiments of the invention are described below on the basis of the drawings, which only serve explanatory purposes and should not be construed as restrictive. In the drawings:

FIG. 8b shows a partial section through the breast shield according to FIG. 8a;

FIG. 9b shows a partial section through the valve body according to FIG. 9a;

FIG. 9c shows a longitudinal section through the valve body according to FIG. 9a;

FIG. 9d shows a view of the valve body according to FIG. 9a;

FIG. 10b shows a view of the adjusting ring according to FIG. 10a;

FIG. 11b shows a partial section through the adapter part according to FIG. 11a;

FIG. 12c shows a longitudinal section through the media separation membrane according to FIG. 12a;

FIG. 13c shows a longitudinal section through the pump membrane according to FIG. 13a;

DESCRIPTION OF PREFERRED EMBODIMENTS

A preferred exemplary embodiment of the breastpump according to the invention is illustrated in FIGS. 1 to 17.

Overview of the Individual Components

Figure 1:
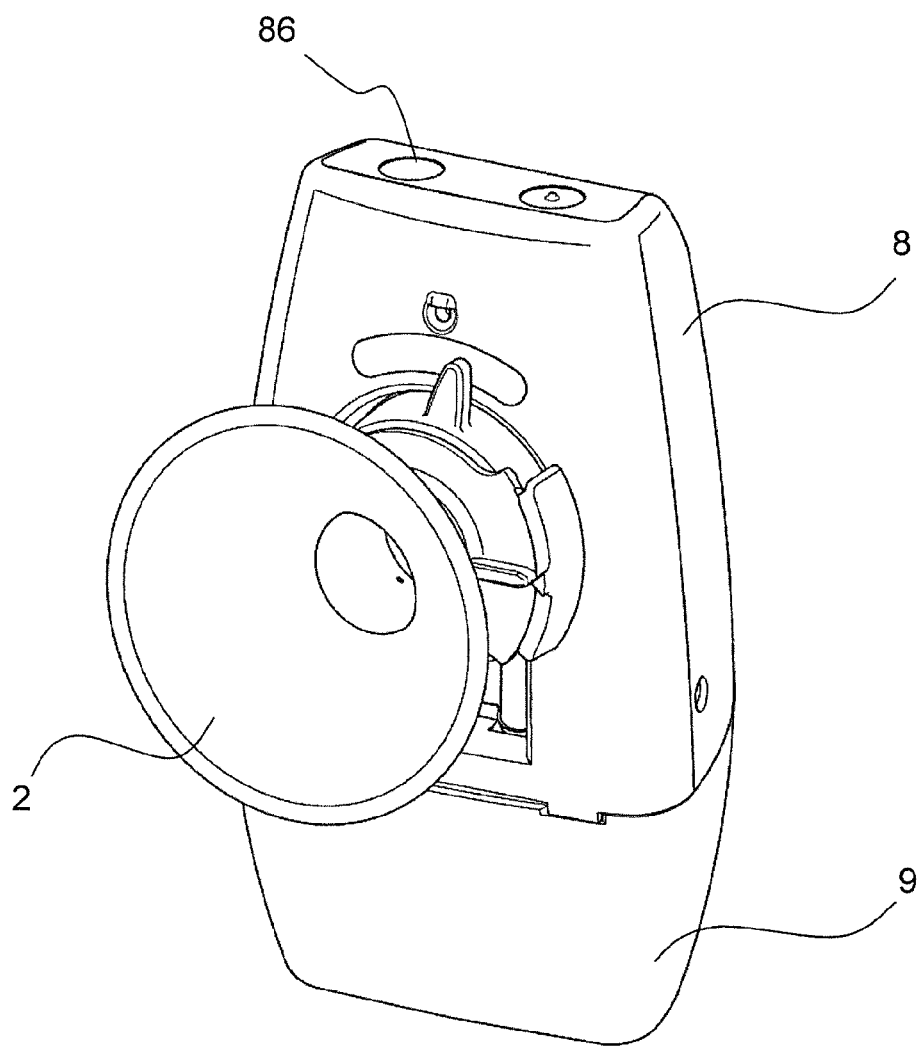
FIG. 1 shows a perspective illustration of a breastpump according to the invention.

As is identifiable from FIG. 1, the breastpump has a compact design. It has a pump housing 8 with a breast shield 2 fastened thereto and a milk collection container 9 that is likewise fastened to the pump housing 8. A motor with a force transmission element, for example a spindle, is arranged in the pump housing 8. Further, at least one electronic controller for controlling the motor, actuation switches 86 for actuating the pump and an energy store are present in the pump housing 8.

Figure 2:
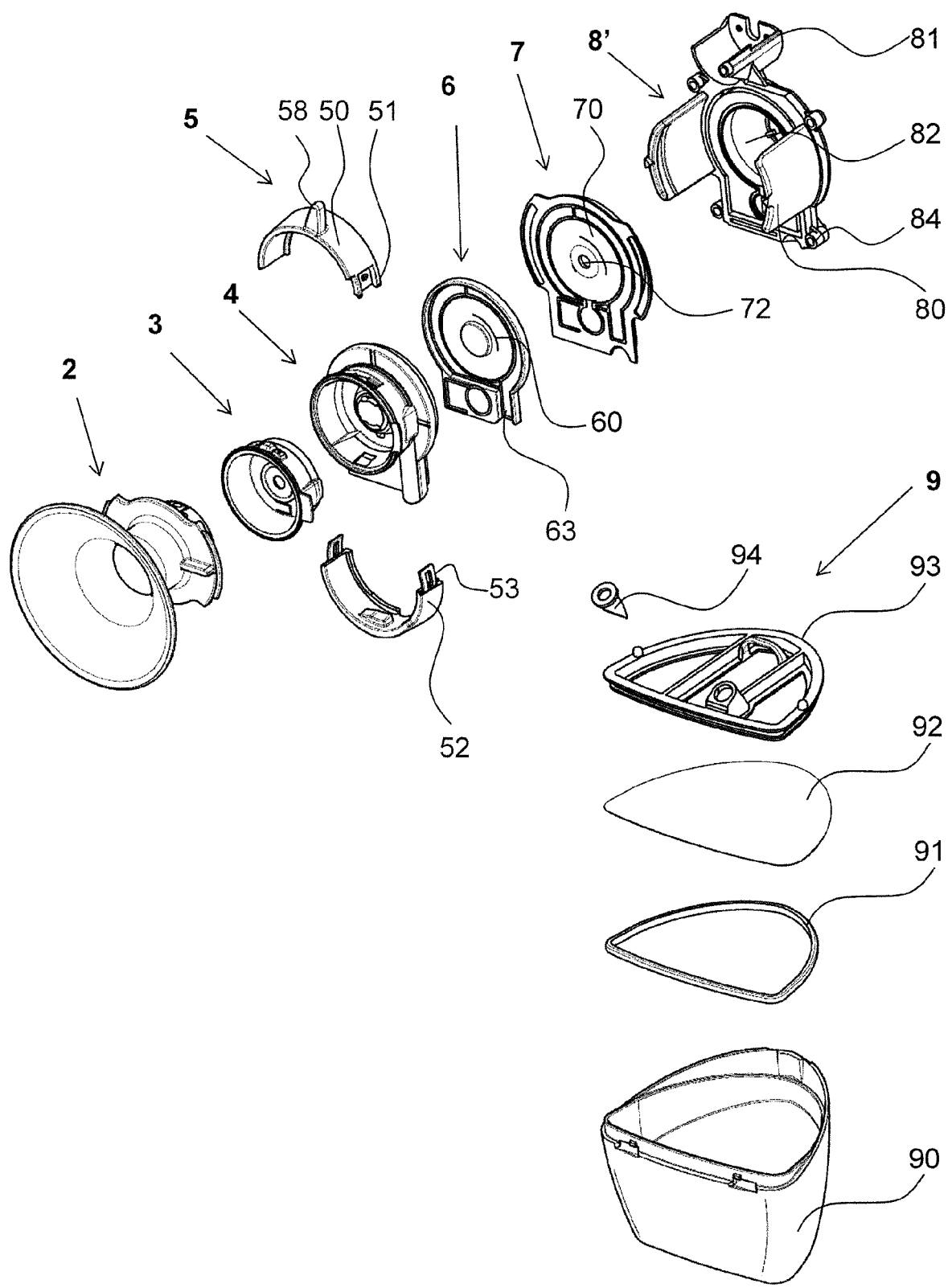
FIG. 2 shows an exploded view of the breastpump according to FIG. 1 in a perspective view.
Figure 3:
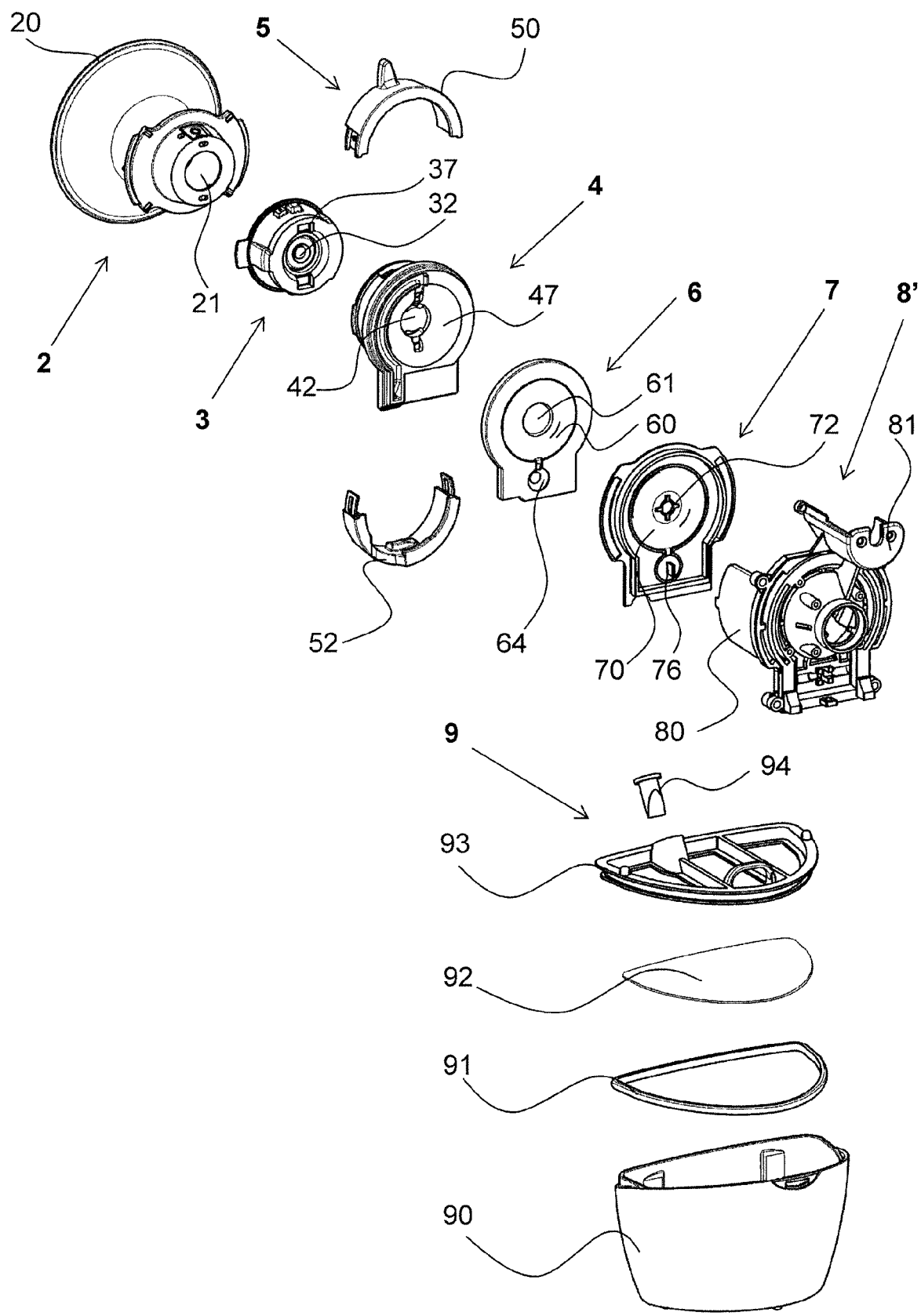
FIG. 3 shows an exploded view of the breastpump according to FIG. 1 in a further perspective view.

FIGS. 2 and 3 show an exploded view of this breastpump. It comprises the aforementioned breast shield 2 for receiving the mother's breast, a valve body 3 made of a flexible material, in particular silicone, an adapter part 4, a two-part adjusting ring 5, a media separation membrane 6, a pump membrane 7, a carrier module 8', which is part of the pump housing 8, and the already mentioned milk collection container 9.

The Milk Collection Container

The milk collection container 9 is preferably able to be latched on the pump housing 8 on the underside of the latter; preferably it can be detachably fastened by swiveling in. Corresponding latching elements 901, 902 are identifiable in FIG. 17. To this end, the pump housing 8 has latching elements fitting thereto, although these are not illustrated here.

Figure 17:
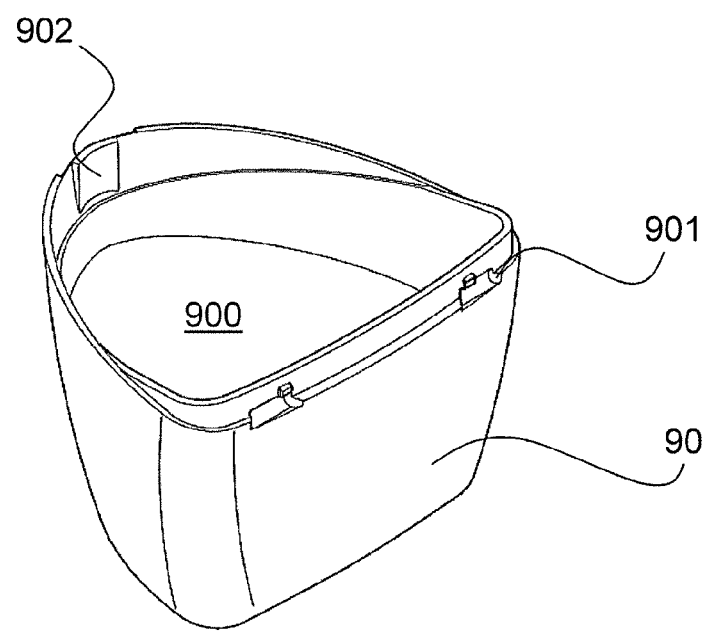
FIG. 17 shows a perspective illustration of a vessel of the milk collection container of the breastpump according to FIG. 1.

The milk collection container 9 comprises a vessel 90 with an interior 900 for receiving the expressed milk (see FIG. 17). This vessel 90 is embodied to be open to the top and can be closed off by a lid. The lid comprises a rigid lower frame part 91, a rigid, semi-rigid or flexible cover 92 and a rigid upper frame part 93. The lower frame part 91 corresponds to the form of the circumference of the opening of the vessel 90 and rests on the latter in sealing fashion. The rigid upper frame part 93 clamps the cover between the lower and upper frame part 91, 93. Preferably, the two frame parts 91, 93 are adhesively bonded to one another, welded on one another or not detachable from one another in a non-destructive manner by any other means. The cover 92 is a film or another membrane-like part, which is air permeable but liquid impermeable. Consequently, air can escape from the vessel 90 but no liquid can emerge.

In terms of its form, the upper frame part 93 preferably likewise corresponds to the form of the vessel 90; in particular, its frame 930 corresponds to the form of the lower frame part 91. It is illustrated in detail in FIGS. 15 and 16. Braces 931 are present in the frame 930 for reinforcement purposes and as a protection for the cover 92. A handle 933 makes lifting the lid easier. Spacer pins 934, which are arranged on the frame 930 and project therebeyond, ensure a distance from the pump housing 8 when the milk collection container 9 is mounted, and so air can escape from the container interior 900 into the surroundings. A valve receptacle 932 is formed onto the upper frame part 93 and said valve receptacle forms the only liquid access into the interior of the vessel 90.

Arranged in this valve receptacle 932, there is a container valve 94, which is embodied as a one-way valve. Hence, when the lid is closed, liquid can only enter the milk collection container 9, but cannot leave therefrom. Preferably, as illustrated here, the container valve 94 is a duckbill valve.

The Hygiene Module

Figure 6:
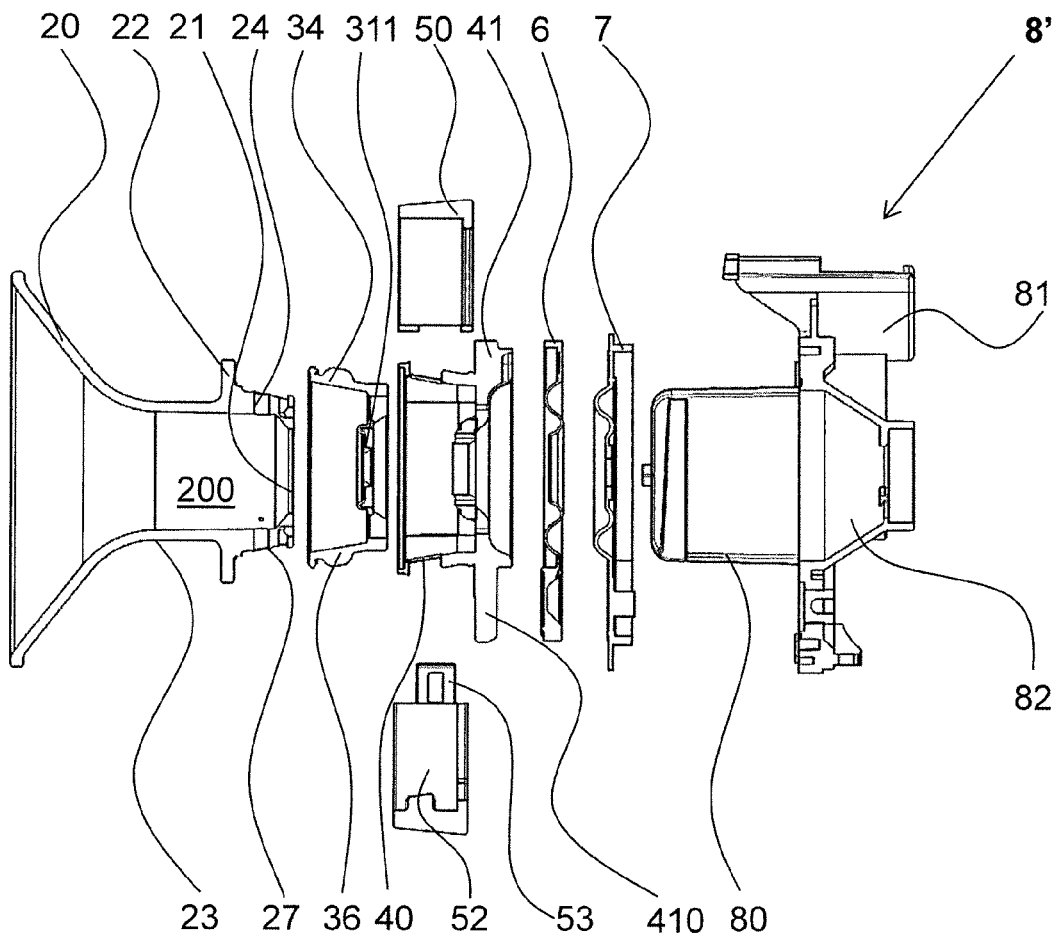
FIG. 6 shows a longitudinal section through a hygiene module, attached to a carrier module of the breastpump according to FIG. 1, in an exploded view.
Figure 7:
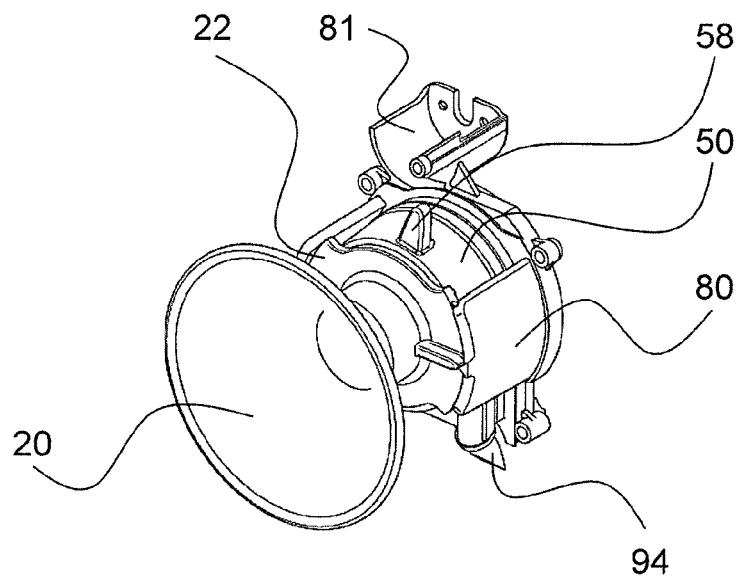
FIG. 7 shows a perspective illustration of the assembled hygiene module according to FIG. 6.

FIGS. 6 and 7 illustrate a hygiene module according to the invention. At least, it comprises the connector 23 of the breast shield 2, the valve body 3, the adapter part 4 and the adjusting ring 5. Moreover, as illustrated here, it may also comprise a flexible media separation membrane 6. If the breast shield has an integral configuration, the entirety thereof is part of the hygiene module.

As illustrated in FIGS. 6 and 7, the aforementioned parts can be assembled to form a common assembly and can be fastened together in the carrier module 8' in a detachable manner. To this end, the connector 23 of the breast shield 2 is preferably fastenable in an interlocking and force-fit manner in corresponding receptacles of the carrier module 8', in two opposing side arms 80 in this case. Preferably, the connection is implemented by way of a bayonet lock, as illustrated here. The connector 23 has a corresponding flange 22, the side arms 80 of the carrier module 8' having corresponding receptacles for the flange and the remaining elements of the bayonet lock.

Thanks to fastening the breast shield to the carrier module 8', and hence to the pump housing 8, the interposed parts, i.e., the valve body 3, the adapter part 4 and the media separation membrane 6 of the hygiene module and the pump membrane 7, are also tightly connected to one another.

The adjusting ring 5 is preferably fastened to the adapter part 4 in a manner that is not non-destructively detachable, with said adjusting ring being swivelable relative to said adapter part about the longitudinal central axis of the hygiene module.

The individual parts of the device and the interaction thereof are described below.

The Breast Shield

Figure 8A:
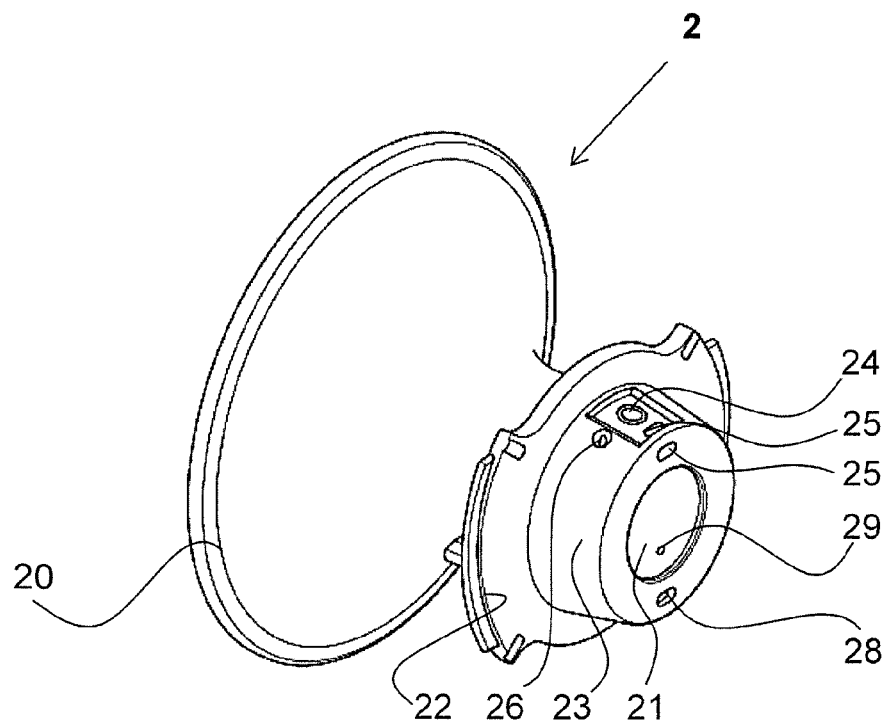
FIG. 8a shows a perspective illustration of a breast shield of the breastpump according to FIG. 1.
Figure 8B:
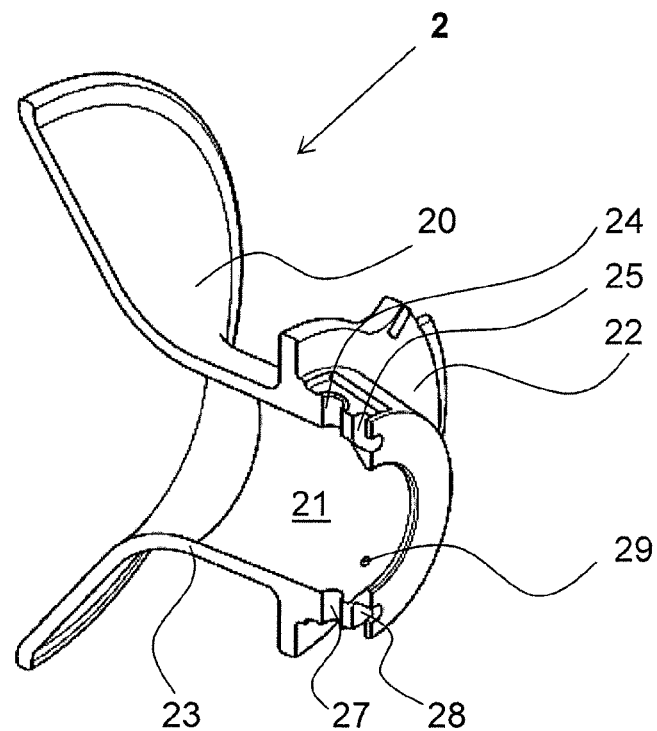
Figure 9A:
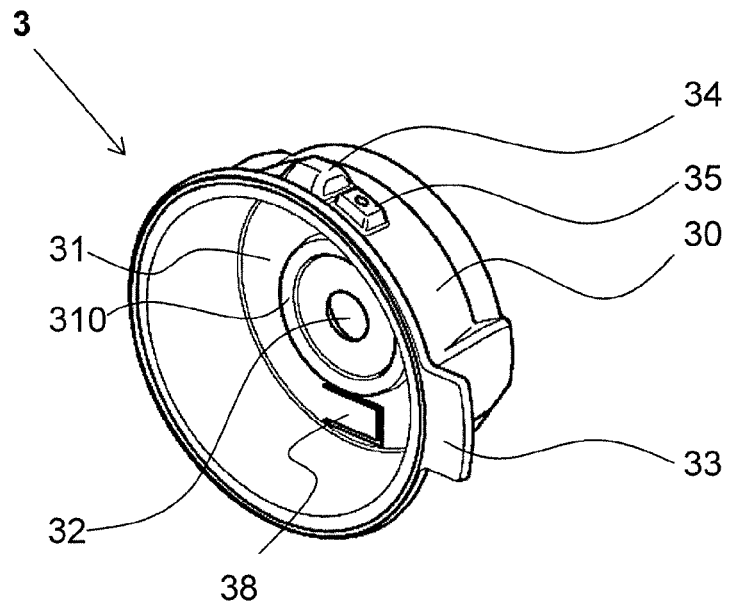
FIG. 9a shows a perspective illustration through a valve body of the breastpump according to FIG. 1.
Figure 9B:
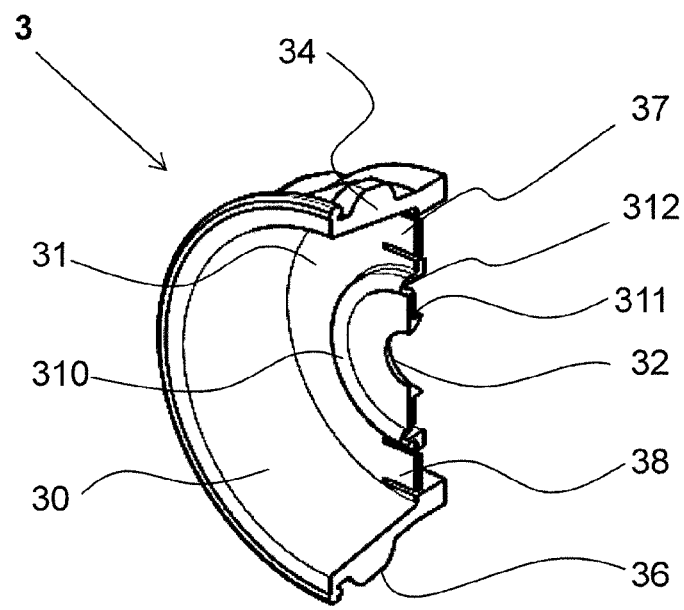
Figure 9C:
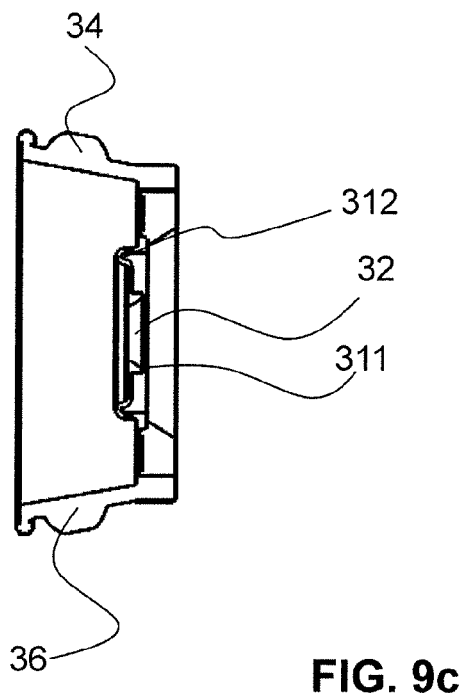
Figure 9D:
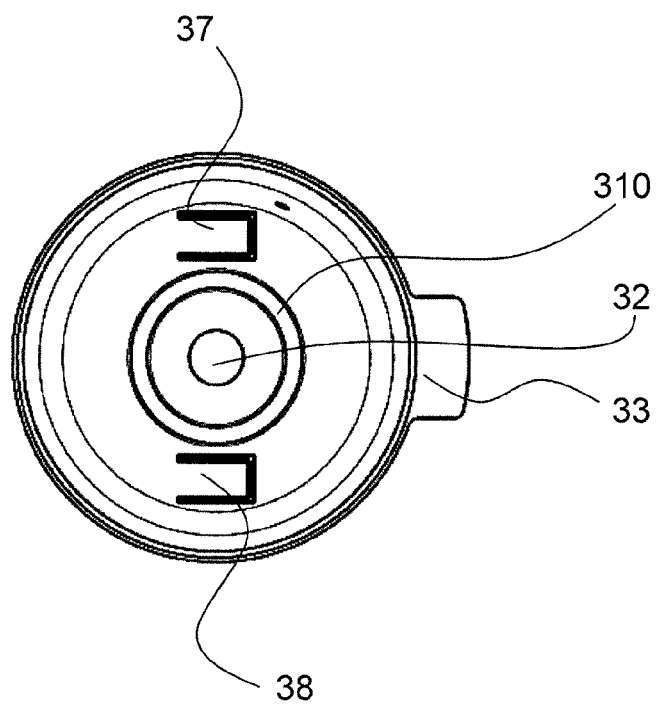

FIGS. 8a and 8b illustrate the breast shield 2. It serves to receive the mother's breast. It comprises a funnel 20 to rest on the mother's breast and an interior 200, cyclically changing negative pressure being appliable to said interior and the mother's breast or at least the nipple being received in said interior.

The breast shield is preferably of integral design and preferably manufactured from a rigid or semi-rigid plastic. However, it may also have a multipart embodiment. Moreover, it can be used with a soft liner, e.g., with a breast shield insert made of soft silicone.

The funnel 20 is followed by a connector 23 with an at least partly circumferential flange 22, the latter forming part of the aforementioned bayonet lock. On the side of the connector 23 facing away from the breast, the interior 200 merges into a passage opening 21, which forms a channel extending along the central longitudinal axis. On the side of the flange 22 facing away from the breast, respectively one recess is present on the connector 23 on two diametrically opposite sides.

A first outlet opening 24 and an angled first flow opening 25 are present in the first recess. The first outlet opening 24 leads from the interior 200 to the outer side of the connector 23, to be precise into the first recess. The first flow opening 25 leads from this first recess in a preferably right-angled channel to the free end face of the connector 23 facing away from the breast. Next to the first outlet opening 24 but outside of the first recess, a first venting opening 26 is present on the circumference of the connector 23. Said venting opening leads from the interior 200 to the outside.

An analogous second recess with a second outlet opening 27 and a second flow opening 28, which have the same embodiments as the first openings, is present on the diametrically opposite side of the connector 23. Moreover, a second venting opening 29 is likewise present outside of the second recess and next to the second outlet opening 27. In actual fact, this second venting opening 29 has no function and it is sealed when the device is used as intended. However, so that the breast shield 2 can likewise be mounted on the carrier module 8' in a position rotated through 180°, all openings are arranged symmetrically.

The Valve Body

FIGS. 9a to 9d show the valve body 3. The valve body 3 is manufactured from a flexible material, preferably from silicone. It preferably has an integral embodiment. It comprises a main body 30 with a hollow cylindrical shape and a rear wall 31. A passage opening 32 is situated centrally in the rear wall. On the side facing away from the breast, the rear wall 31 comprises a furrow 312 that encircles the passage opening 32 in a ring-shaped manner, said furrow forming a sealing area 310 on the opposite side facing the breast. The circumferential edge of the passage opening 32 is provided with a circumferential sealing lip 311 on the side facing away from the breast (see FIGS. 9b and 9c). Consequently, the region of the rear wall 31 within the circumferential sealing area 310 forms a valve which, as explained further below, serves as a baseline vacuum valve.

On the side facing the breast, the main body 30 has a radially protruding positioning lug 33. A first stud 34 and a venting stud 35 are present on the lateral surface of the main body 30. A second stud 36 is situated diametrically opposite thereto. The three studs protrude radially to the outside. The first stud 34 and the second stud 36 have a solid, i.e., non-hollow, embodiment. The venting stud 35 has a passage opening from the interior of the main body 30 to the outside.

Valve flaps that likewise lie diametrically opposite one another are present in the rear region of the rear wall 31 between the sealing area 310 and the lateral surface of the main body 30. A first of these valve flaps has been provided with the reference sign 37; a second of these valve flaps has been provided with the reference sign 38. They preferably are on the same diagonal as the first and the second stud 34, 36.

The Adjusting Ring

Figure 10A:
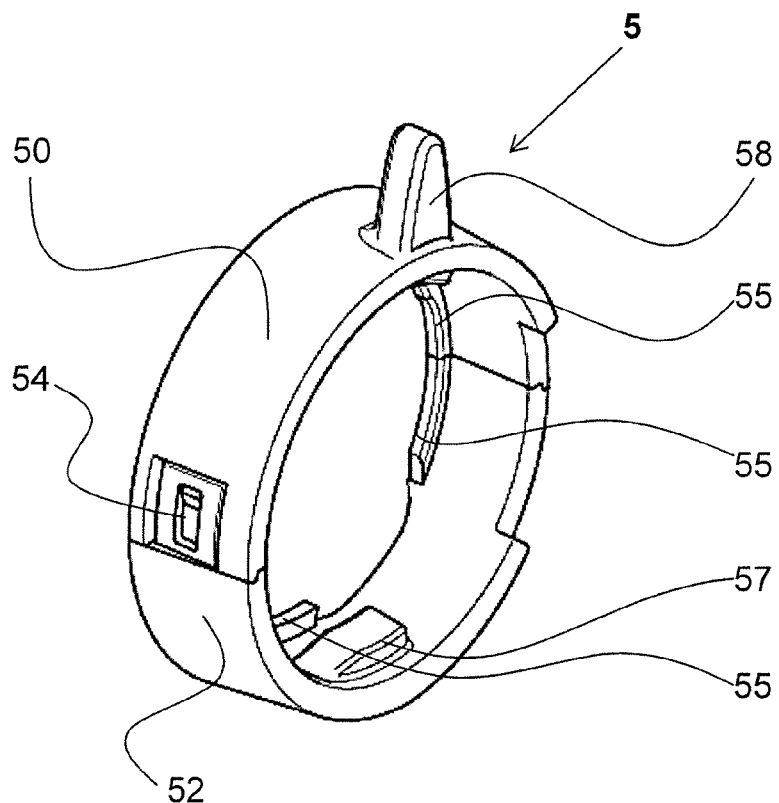
FIG. 10a shows a perspective illustration of an adjusting ring of the breastpump according to FIG. 1.
Figure 10B:
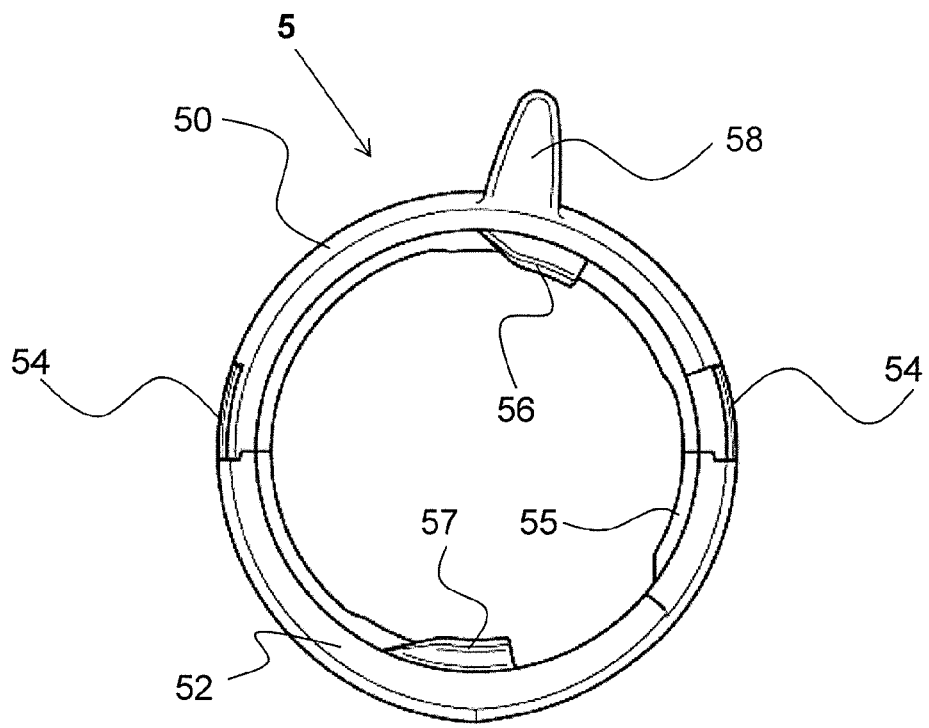

FIGS. 10a and 10b show the adjusting ring 5. It is preferably rigid and preferably made of plastic. The adjusting ring 5 preferably consists of two parts. A first part 50 has the form of a half-ring and it is provided with a first connector part 51 at both free ends. The second part 52 likewise has the form of a half-ring and it is provided at its free ends with respectively one second connector part 53. The first and second part 50, 52 form a common ring and the two connector part pairs 51, 53 are provided with latching elements 54 in order to connect these to one another, preferably in non-detachable fashion. A partly circumferential stop 55 that protrudes radially to the inside is present at the inner circumference of the ring, said stop preventing a new removal of the adjusting ring 5 after mounting on the adapter part 4. A first and a second pressure element 56, 57 are formed at the inner wall of the adjusting ring. These are preferably elevations that protrude radially to the inside and which merge into a surface extending parallel to the ring inner surface via an angled surface, which is also referred to as a ramp. An outwardly projecting actuation lever 58 is formed onto the first part 50.

The Adapter Part

Figure 11A:
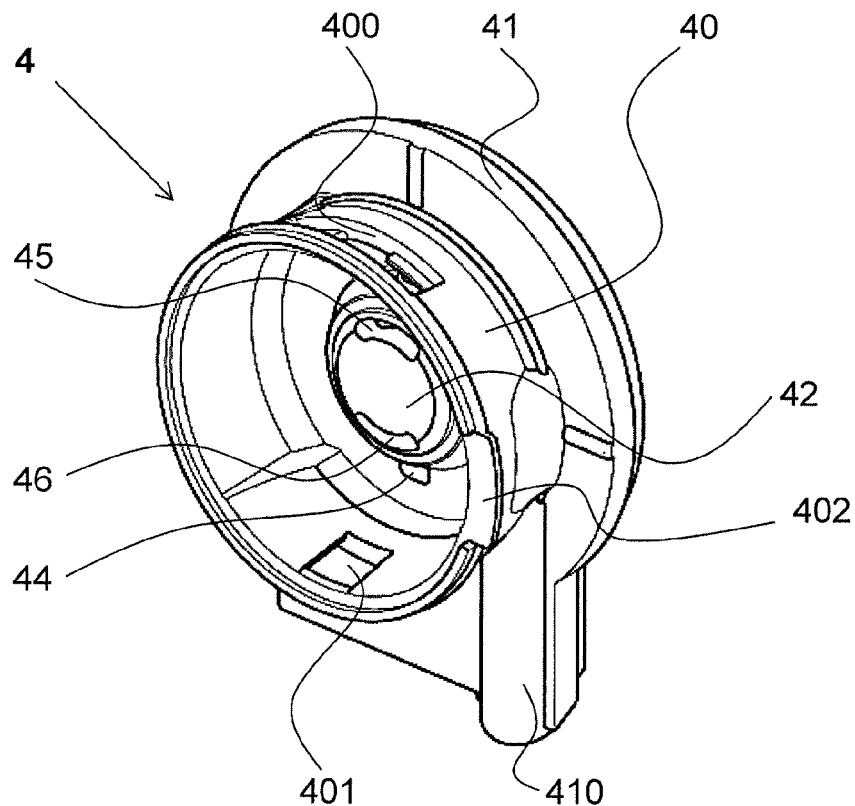
FIG. 11a shows a perspective illustration of an adapter part of the breastpump according to FIG. 1 from a first side.
Figure 11B:
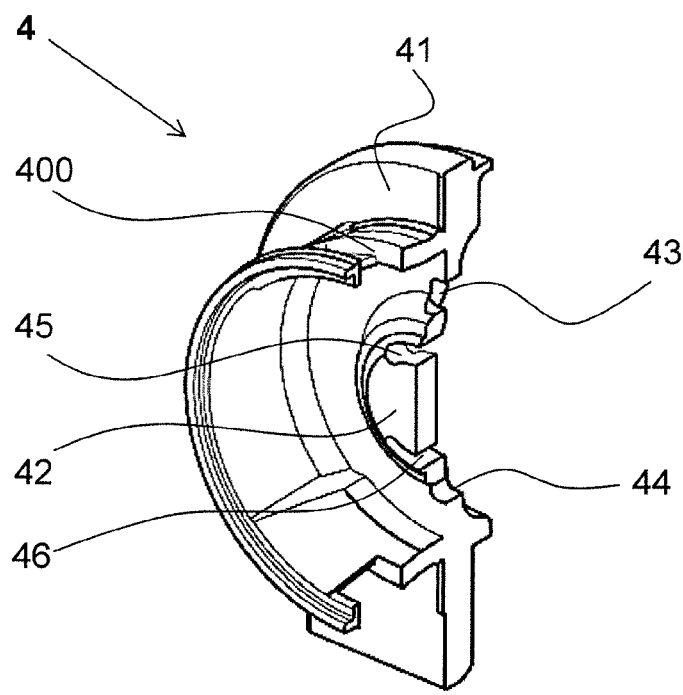
Figure 11C:
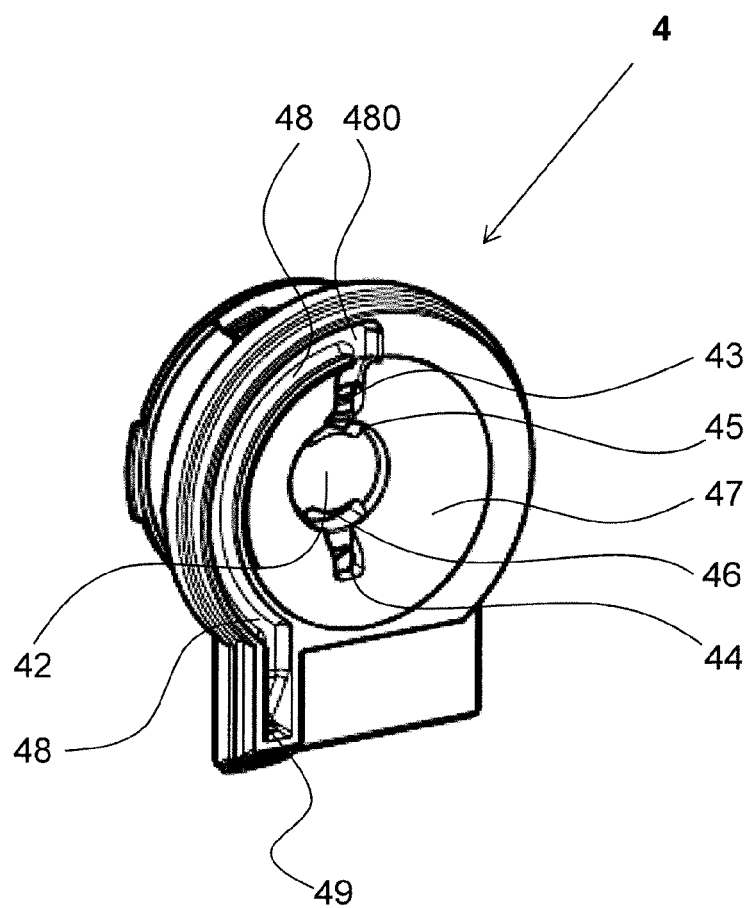
FIG. 11c shows a perspective illustration of the adapter part according to FIG. 11a from a second side.

FIGS. 11*a* to 11*c* show the adapter part 4. It preferably consists of a rigid material, preferably of plastic. It has a hollow-cylinder-shaped main body 40 with a substantially closed, flange-like pump-side wall 41. In its lateral surface, the main body 40 has a first window 400 and a diametrically opposite second window 401. A positioning aid 402 is present on the end face of the main body 40 that is close to the breast shield, said positioning aid forming the counterpiece to the positioning lug 33 of the valve body 3 and, together with the positioning lug 33, serving to position the valve body 3 in a manner secured against rotation.

The pump-side wall 41 extends in a direction, which is referred to as down here, into a channel wall 410. Further, the pump-side wall has an elevated central wall part 42, which protrudes into the region that is close to the breast shield. Consequently, a concave area is formed on the opposite side of the wall part 42, i.e., facing the pump housing, said concave area forming the already mentioned rigid cup and being part of the pump chamber 47.

A first passage opening 43 and a second passage opening 44 are present between the elevated wall part 42 and the lateral surface of the main body 40 in the pump-side wall 41. The two passage openings 43, 44 lie diametrically opposite to one another. In this example, they have a circular embodiment. In the edge region of the elevated wall part 42, but already on its elevated area, a first backwash opening 45 and a second backwash opening 46 are present. These preferably have an elongate embodiment. These openings all lead into the pump chamber 47.

As may be identified in FIG. 11*c*, the concave cup of the pump chamber 47 is surrounded by a circumferential plane edge, said cup serving as a sealing area. A groove 48, which preferably starts at an uppermost point of the pump chamber 47 and which has a fluid-communicating connection therewith via an outlet opening 480, extends in this edge. The groove 48 extends downward along the circumference of the pump chamber 47, here in the shape of a partial circle, to an outlet 49. The outlet 49 is situated in the channel wall 410.

The Media Separation Membrane

Figure 12A:
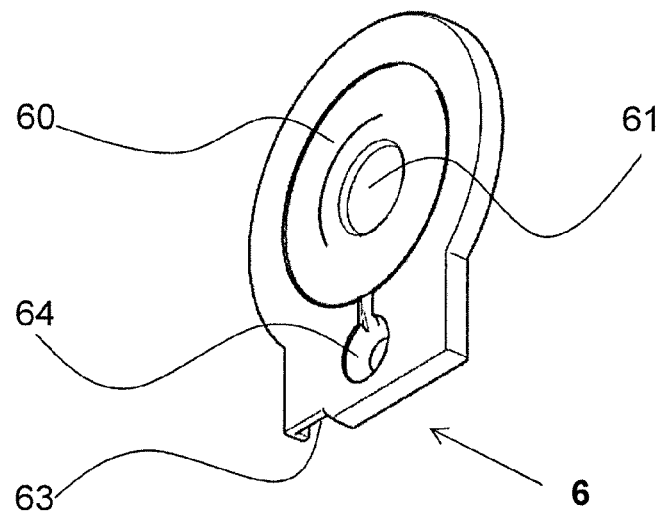
FIG. 12a shows a perspective illustration of a media separation membrane of the breastpump according to FIG. 1 from a first side.
Figure 12B:
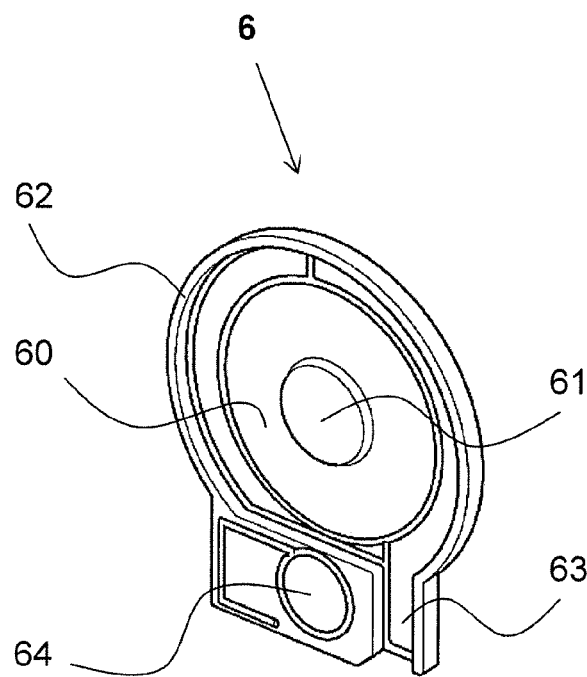
FIG. 12b shows a perspective illustration of the media separation membrane according to FIG. 12a from a second side.
Figure 12C:
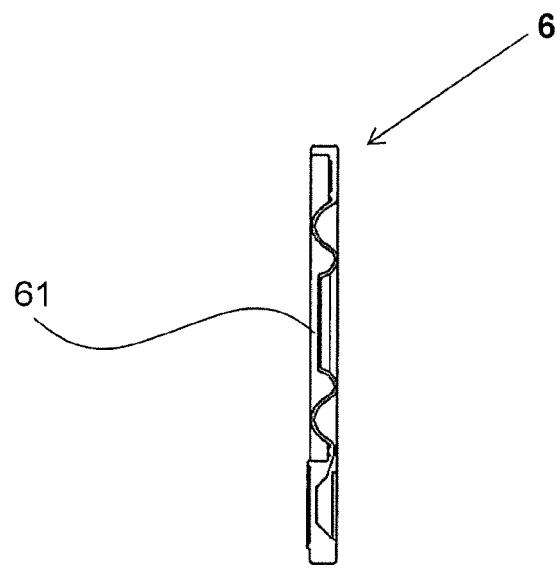

FIGS. 12*a* to 12*c* illustrate the media separation membrane 6. It is embodied to be flexible, preferably manufactured in integral fashion and preferably manufactured from silicone. It has a membrane area 60, which is preferably provided with at least one ring-shaped furrow in a manner known per se. A central region 61 of the membrane area preferably has an elevated embodiment and faces the adapter part 4. The edge of the membrane area 60 is embodied as a sealing area 62 and it rests, in sealing fashion, on the edge of the adapter part 4, as a result of which the pump chamber 47 is formed. A groove 63 extends within the sealing area 62 along the circumference of the media separation membrane 6 and forms the sealing closure of the groove 48 of the adapter part 4. A recess 64 in the lower region of the media separation membrane 6, said recess facing the pump housing, serves as a clear space for a pressure sensor, which will still be described below.

Preferably, as illustrated in the figures, the media separation membrane 6 has reinforcements in the form of ribs, which ensure the functionality of the media separation membrane. That is to say, the ribs ensure that the membrane moves as desired and nevertheless always rests in sealing fashion against its neighboring parts.

The Pump Membrane

Figure 13A:
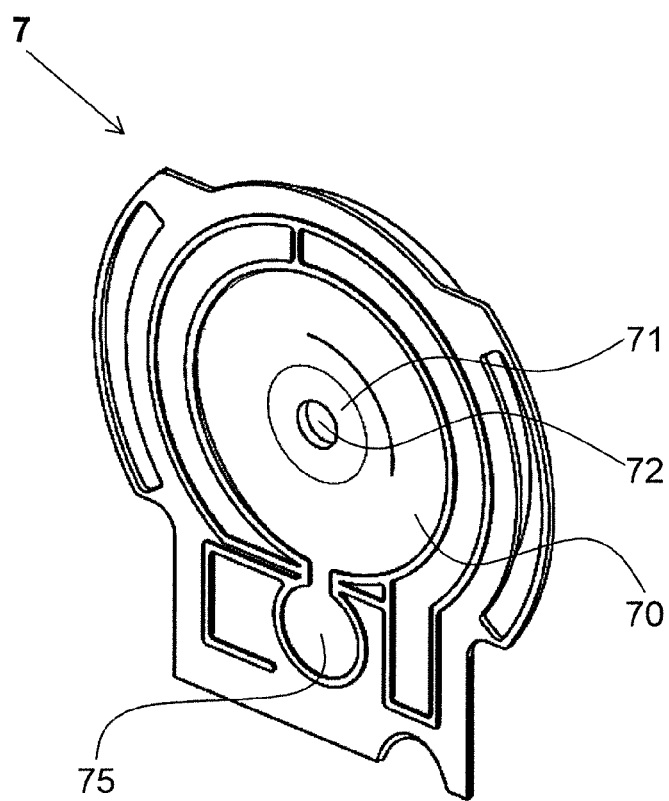
FIG. 13a shows a perspective illustration of a pump membrane of the breastpump according to FIG. 1 from a first side.
Figure 13B:
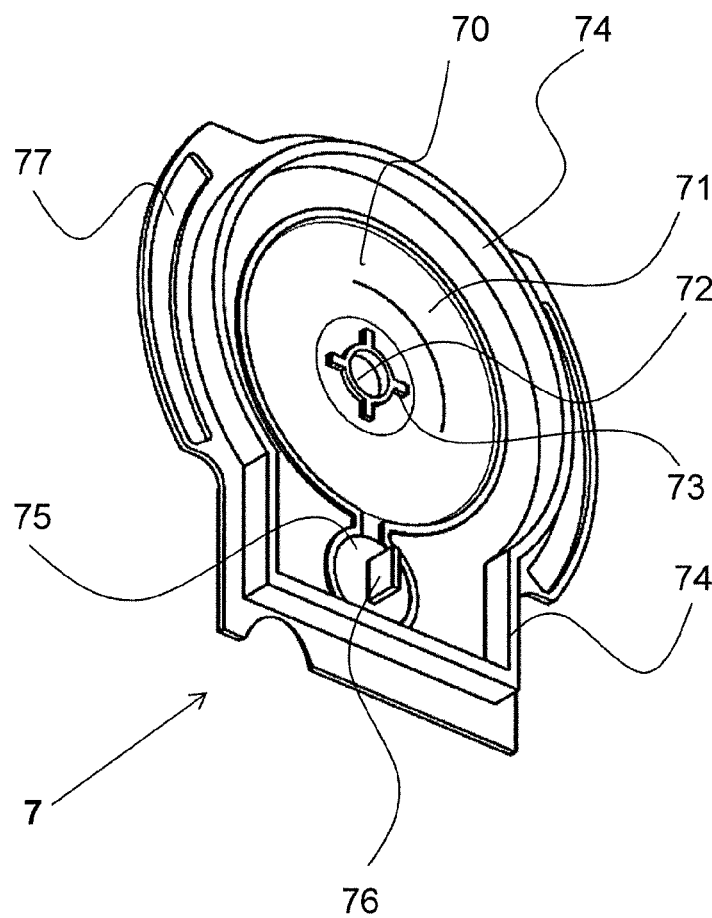
FIG. 13b shows a perspective illustration of the pump membrane according to FIG. 13a from a second side.
Figure 13C:
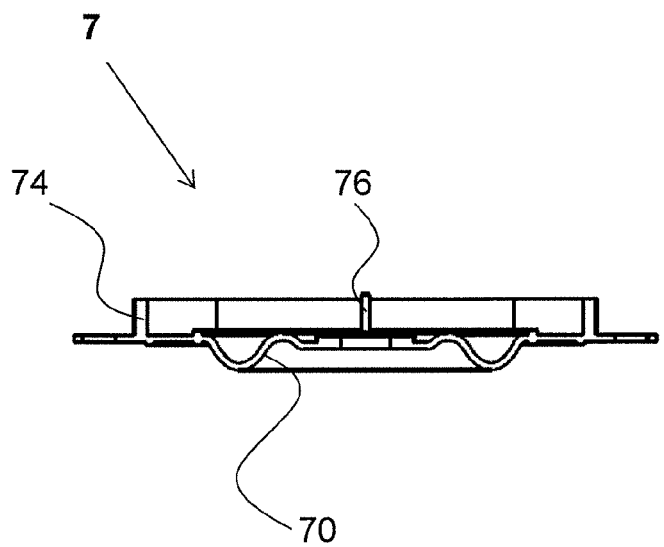

FIGS. 13*a* to 13*c* illustrate the pump membrane 7. It, too, has a membrane area 70 and a central region 71. In contrast to the whole-area media separation membrane 6, the central region 71 of the pump membrane 7 is provided with a passage opening 72, the edge region of which preferably comprises a reinforcement 73, here in the form of ribs. Once again, a circumferential sealing area 74 is present, the latter resting in sealing fashion on the corresponding area of the carrier module 8' in the assembled state of the device. Side wings 77 are situated outside of the sealing area 74. Together with the circumferential plane sealing area 74 (FIG. 13*b*), the side wings 77, in the assembled state, form a tight barrier for liquids acting from the outside and consequently protect the electronics.

The lower region of the pump membrane 7, which, however, is still situated within the closed circumferential sealing area 74, is embodied as a pressure sensor. The pressure sensor comprises a sensor area 75 in the form of a membrane, which is connected to the membrane area 70 via a connecting web, and a vane 76, which protrudes in perpendicular fashion from the sensor area in the direction of the pump housing. This type of pressure sensor is described in WO 2013/049944 A1.

As may be identified in the figures, the media separation membrane 6 and the pump membrane 7 have similar forms, in particular in respect of their movable regions for producing the negative pressure.

The Carrier Module

Figure 14:
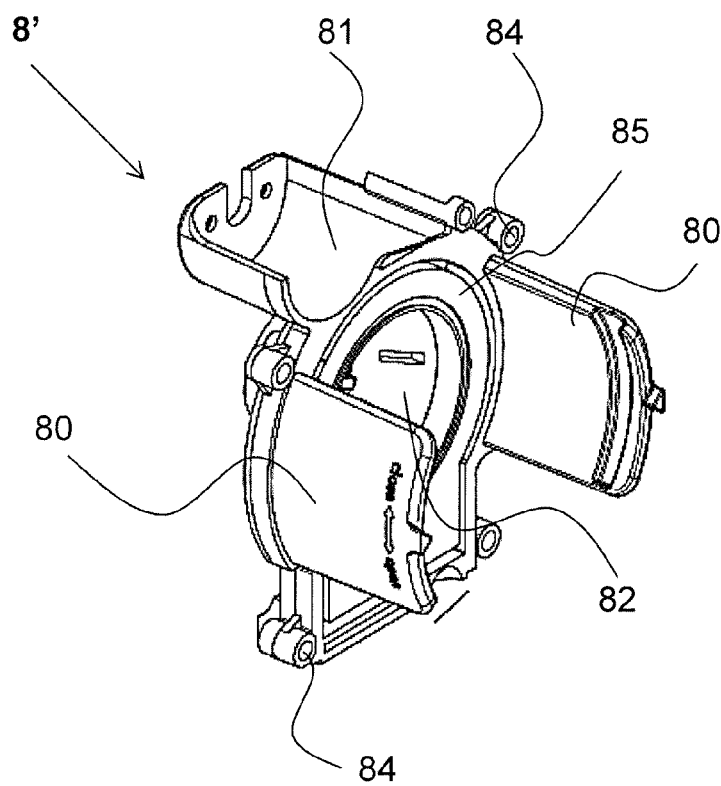
FIG. 14 shows a perspective illustration of a carrier module of the breastpump according to FIG. 1.
Figure 15:
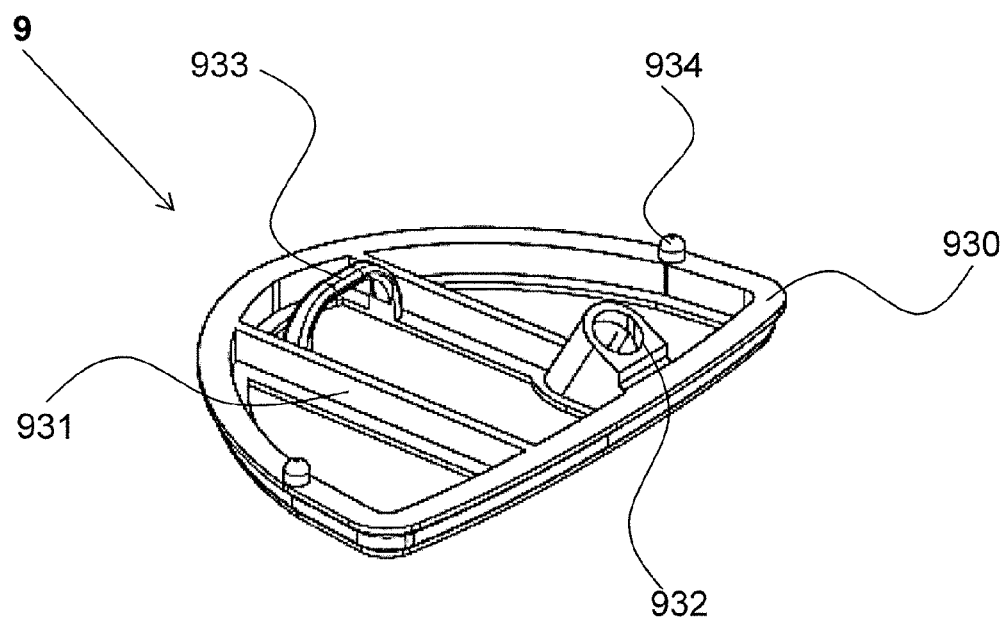
FIG. 15 shows a perspective illustration of an upper frame part of a milk collection container of the breastpump according to FIG. 1.
Figure 16:
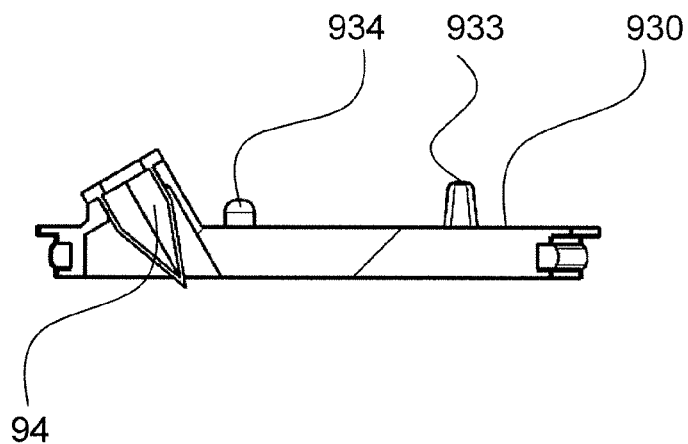
FIG. 16 shows a longitudinal section through the upper frame part according to FIG. with a container valve.

The carrier module 8' is illustrated in FIG. 14. It is held in an outer housing of the pump housing. The outer housing is visible in FIG. 1. Preferably, the carrier module 8' is screwed into this outer housing. The corresponding fastening holes are provided with the reference sign 84. The carrier module can be produced in integral fashion from plastic. However, it may also have a multipart embodiment and/or be manufactured from a different material. The carrier module 8' comprises two protruding side arms 80 with a bayonet lock for receiving the breast shield 2. The side arms are arranged laterally on a spindle receptacle 82. The spindle receptacle 82 has a passage opening and a circumferential edge 85, which forms the counterpiece to the sealing area 74 of the pump membrane 7. A motor receptacle 81 in the form of a cup is formed on the spindle receptacle 82. The motor receptacle 81 serves to hold an electric motor, which is connected to a spindle 83 (see FIG. 4).

Mode of Operation of the Assembled Assembly

FIG. 6 allows identification of how the individual openings and valves interact.

The valve body 3 can be inserted, positioned in terms of rotation, into the hollow-cylindrical main body 40 of the adapter part 4. Here, the adjusting ring 5 is already non-detachably connected to the adapter part 4, with the first pressure element 56 protruding to the inside through the first window 400 and the second pressure element 57 protruding to the inside through the second window 401. The first stud 34 of the valve body 3 is situated in this case below the first window 400 and the second stud 36 is situated above the first window 401. The valve flaps 37, 38 of the valve body 3 are respectively situated over the first and second passage opening 43, 44 of the adapter part. The sealing lip 311 rests in sealing fashion on the elevated wall part 42, wherein the first and the second backwash opening are arranged in a sealed ring region between the furrow 312 and the sealing lip 311.

Should the breast shield 2 now be inserted, the first stud 34 lies over the first outlet opening 24 and the venting stud 35 lies over the first venting opening 26. The second stud 36 lies over the second outlet opening 27. The second venting opening 29 is covered by the lateral surface of the valve body 3 and consequently closed off.

If the breast shield 2 is now connected to the carrier module 8', the individual connections are created between the described channels and openings and sealed to the outside.

Figure 4:
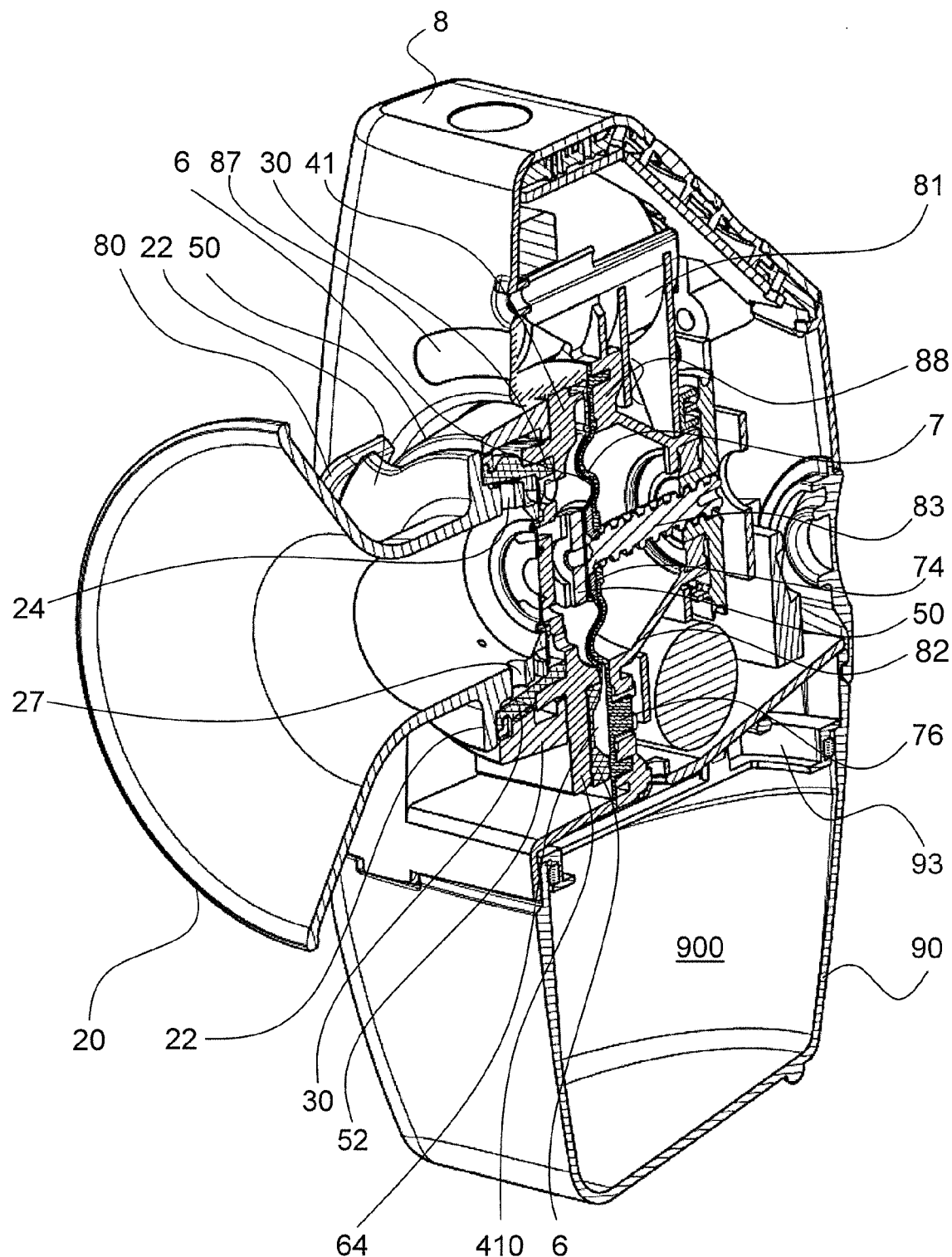
FIG. 4 shows a partial section through the breastpump according to FIG. 1 in a first perspective view.
Figure 5:
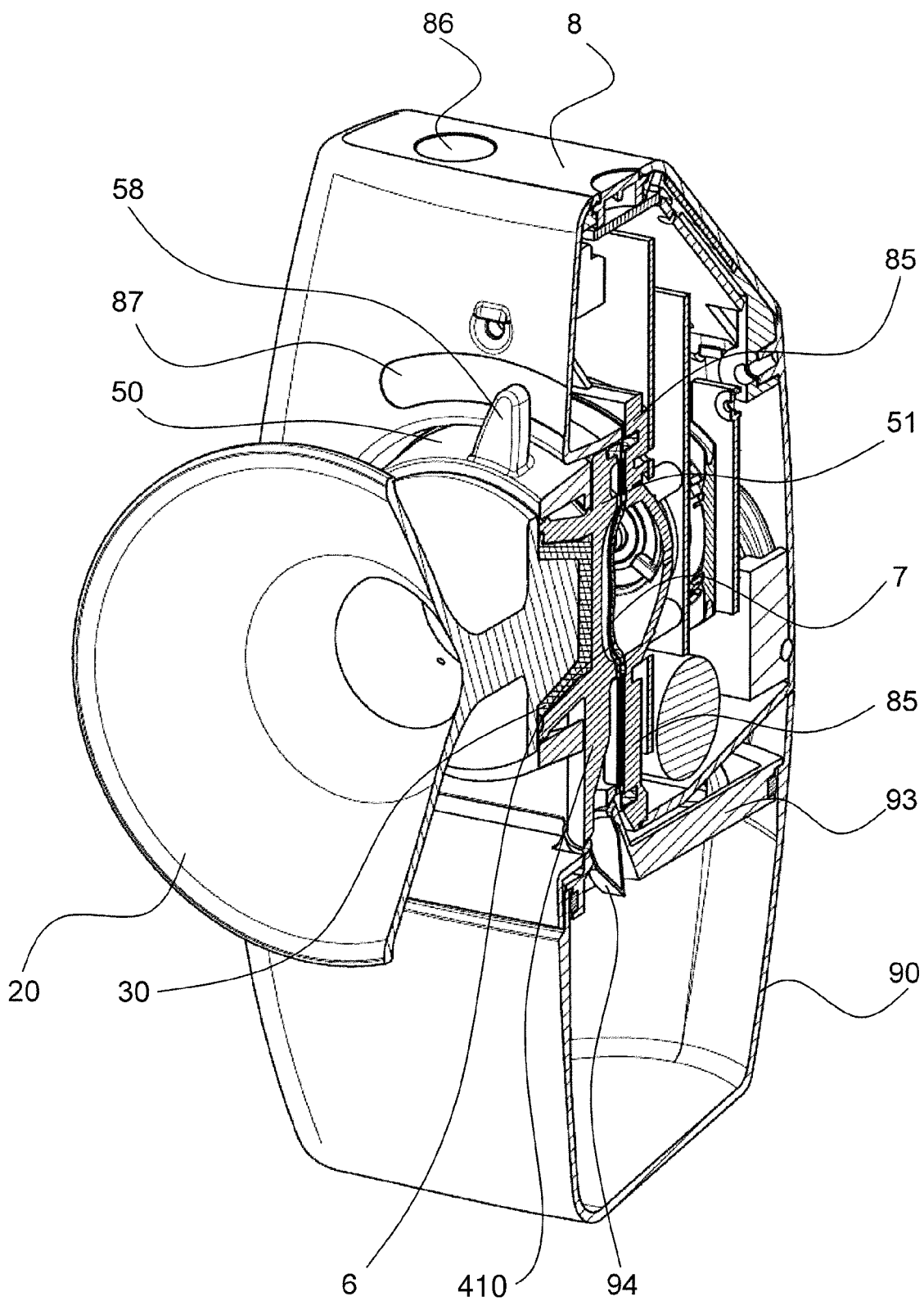
FIG. 5 shows a partial section through the breastpump according to FIG. 1 in a second perspective view.

FIGS. 4 and 5 illustrate the breastpump according to the invention in the assembled state. As can easily be identified, this system has practically no dead space.

The spindle 83 that drives the pump membrane 7 is identifiable in FIG. 4. The media separation membrane 6 has a form which nestles against the pump membrane 7 such that both membranes 6, 7 move together and no losses occur here either. The pump housing 8, more precisely the carrier module 8', comprises a rear wall 88, against which the pump membrane 7 rests in sealing fashion when the hygiene module is fastened to the carrier module 8'. This can easily be identified in FIGS. 4 and 5. The adjusting ring 5 is arranged in swivelable fashion within the side arms 80, wherein the actuation lever 58 also serves as an indication element. It moves along a display 87, which is attached to the pump housing 8, and consequently provides the user with information about the position of individual valves and consequently provides information about the operational state of the pump. That is to say, whether the pump is operationally ready for expressing or whether it is in the draining state is indicated. This will be explained below.

Individual valves can be opened and closed manually by rotating the adjusting ring 5. More precisely, the first outlet opening 24 can be manually opened and closed together with the first flow opening 25 as an alternative to the second outlet opening 27 together with the second flow opening 28. The first venting opening 26 is opened and closed together with the second outlet opening 27 and the second flow opening 28. The second venting opening 29 always remains closed on account of its position within the valve body 3.

Naturally, the second venting opening is opened and closed instead of the first venting opening should the breast shield 2 be positioned relative to the valve body 3 in such a way that the second openings are situated at the position of the first openings.

In a first position, which is chosen at the start of the expressing process and during the entire expressing process, the second stud 36 of the valve body 3 is pressed downward by the second pressure element 57 of the adjusting ring and said stud rests on the recess and consequently rests on the second outlet opening 27 and the second flow opening 28 of the breast shield 2. Moreover, the venting stud 35 is pressed onto the first venting opening 26, and closes off the latter, by way of the first pressure element 56. By contrast, the first stud 34 of the valve body 3 is released such that the first outlet opening 24 and the first flow opening 25 form a fluid-communicating channel from the interior 200 of the breast shield to the main body 30 of the valve body 3. This can be identified best in FIGS. 2, 3 and 6.

The adjusting ring 5 is rotated in a second position. The first pressure element 56 releases the venting stud 35, and consequently the first venting opening 26, but, by contrast, presses the first stud 34 onto the recess and consequently closes off the first outlet opening 24 and the first flow opening 25. The second pressure element 57 moreover releases the second stud 36, and so the second outlet opening 27 and the second flow opening 28 now form an open, continuous channel from the interior 200 of the breast shield 2 to the valve body 3. The second outlet opening 27 and the second flow opening 28 form a draining channel, which will still be described in more detail below.

The reciprocal opening and closing is preferably implemented at the same time. However, it is also possible to arrange the pressure elements with such an offset that all openings are closed off in an intermediate state.

Expressing Breastmilk and Emptying Process

So that milk can be expressed from the mother's breast, the actuation lever 58, and consequently the adjusting ring 5, is brought into the aforementioned first position. The pump membrane 7, together with the media separation membrane 6, is moved to the adapter part 4 and back again by means of the drive such that negative pressure arises in the pump chamber 47 and in the interior 200 of the breast shield 2. Here, the vacuum line from the pump chamber 47 into the interior 200 of the breast shield 2 is formed by the first passage opening 43 in the adapter part 4, the opening in the valve body 3 covered by the first valve flap 37 and the channel formed by the first flow opening 25 and the first outlet opening 24 in the breast shield.

The baseline vacuum valve, formed, inter alia, by the sealing lip 311 of the valve body 3, renders it possible to maintain a baseline negative pressure in the interior 200 of the breast shield 2 when the pump stroke runs in the direction of atmospheric pressure. The baseline vacuum valve opens during the pump stroke in the direction of atmospheric pressure and only closes once a predetermined minimum pressure in the interior 200 has been reached. The mode of operation is explained once again in more detail below on the basis of a scheme. The return flow of the air into the breast shield 2 is implemented by way of the first and the second backwash opening 45, 46 of the adapter part 4, the passage opening 32 of the valve body 3 and the passage opening 21 of the breast shield 2.

By applying this vacuum to the mother's breast, the latter is stimulated and milk flows from the breast into the interior 200 of the breast shield 2. The interior 200 fills until the fill level of the milk reaches the first outlet opening 24. Here, the breast shield 2 is preferably held in such a way that this first outlet opening 24 is situated in an upper region of the breast shield 2.

The expressed milk then flows through the channel, formed by the first outlet opening 24 and the first flow opening 25, and through the opening covered by the first valve flap 37 into the adapter part 4, where it reaches the pump chamber 47 through the first passage opening 43.

The pump chamber 47 likewise fills with milk until the outlet opening 480, which is arranged at the top, is reached. Subsequently, the milk flows through the channel, formed by the groove 48 of the adapter part 4 and the groove 63 or the cover of the media separation membrane 6, and out of the hygiene module through the outlet 49 and into the milk collection container 9 through the container valve 94.

When the pump stroke respectively from producing a negative pressure in the direction of atmospheric pressure, the baseline vacuum valve opens first and facilitates a partial return flow of the air or the milk to interior 200. This partial return flow is implemented by the first and second backwash opening 45, 46, the open baseline vacuum valve, the passage opening 32 and the passage opening 21. The valve closes at a certain vacuum value in the interior, and so the pressure cannot increase further in the direction of atmospheric pressure.

When the mother wishes to terminate the expression of milk or if no more milk flows from the breast, the mother swivels the adjusting ring 5 into the second position. The previously used vacuum and milk channel is closed off by virtue of the first outlet opening 24 and the first flow opening 25 being closed off. However, the second outlet opening 27, the second flow opening 28 and the first venting opening 26 open in the process. This change can be implemented with a running pump, i.e., with the pump membrane 7 still being driven. Additionally, the pump can be deactivated to this end and subsequently be put into operation again. Since the pump continues to suck, the milk already expressed from the mother's breast and still situated in the interior 200 of the breast shield 2 is pumped through the second outlet opening 27, the second flow opening 28, the opening of the valve body 3 covered by the second valve flap 38 and the second passage opening 44 of the adapter part 4 and into the pump chamber 47. From there, it is displaced from the pump chamber 47 in the direction of the outlet opening 480 by the movement of the pump membrane 7 and the media separation membrane 6. Consequently, it likewise flows through the groove 48 and the outlet 49 into the milk collection container 9. This allows almost complete draining of both the interior 200 of the breast shield 2 and the pump chamber 47. Moreover, the device can be placed at an angle in order to drain the entire milk from the system into the milk collection container 9.

It should be noted that the breast pump is preferably held in such a way at the start of the expressing process that the first outlet opening 24 of the breast shield and the outlet opening 480 of the pump chamber 47 are situated in an upper region of the respective cavity. As a result, air can escape from the system and the two hollow chambers are filled relatively quickly with milk. This facilitates a change that is as fast as possible from a purely pneumatic pump system with air as a working fluid into a purely or predominantly hydraulic pump system, in which milk forms the working fluid or at least forms a large portion of the working fluid. However, it is not mandatory for the openings to be arranged in such a way at the start of the expressing process. The change from one pump system into the other simply requires a longer period of time and/or cannot be carried out completely.

As soon as the milk has partly flooded the interior 200 and the pump chamber 47, preferably up to the aforementioned openings, the breastpump can be brought into any position. This applies not only to the breast shield 2 and the pump chamber 47, but also, in particular, to the milk collection container 9. Thanks to the container valve 94 that is embodied as a check valve and thanks to the liquid-impermeable cover 92, the milk collection container 9 can even be put on its head without impairing the operation of the breastpump.

In preferred embodiments, the breast shield and the adjusting ring, too, are illuminated so that the mother can also implement a visual inspection during expressing at night.

The above-described breast pump is merely an exemplary embodiment, in which the principle according to the invention can be implemented and the method according to the invention can be applied. Therefore, FIGS. 18 to 23c once again schematically illustrate the core of the concepts according to the invention.

Fundamental Principle

FIG. 1 schematically illustrates the breast shield 2 with the interior 200. The breast shield 2 rests on a mother's breast in sealing fashion; the nipple W protrudes into the interior 200. The interior 200 is connected to a pump chamber 47 via an outlet opening 16. An additional draining opening 19 likewise leads from the interior 200 to the pump chamber 47. The outlet opening 16 is provided with a pump valve 12; the draining opening is provided with a draining valve 14. A baseline vacuum valve 13 closes a third opening 17 between the pump chamber 47 and the interior 200 of the breast shield 2. Moreover, a venting opening that is able to be closed off by a venting valve 11 leads from the interior 200 of the breast shield 2 to the outside.

The volume of the pump chamber 47 is modifiable by means of a pump means 10, for example a pump membrane or piston. The pump means 10 is driven, for example by means of a spindle 100.

An outlet opening 480 leads from the pump chamber 47 into a milk collection container 9. The inlet into the milk collection container 9 is preferably provided with a check valve, which is referred to as container valve 94 here. The milk collection container 9 is vented; preferably, an inlet 95 with an inlet valve 96 is present to this end.

The comparison with the exemplary embodiment described above in detail shows that the venting opening 15 and the venting valve 11 correspond to the first venting opening 26, the venting stud 35 and the first pressure element 56.

The outlet opening 16 and the pump valve 12 of the schematic illustration correspond to the first outlet opening 24, the first flow opening 25, the first stud 34, the first pressure element 56 and the first valve flap 37 of the specific exemplary embodiment.

The draining opening 19 and the draining valve 14 of the schematic illustration correspond to the second outlet opening 27, the second flow opening 28, the second stud 36, the second pressure element 57 and the second valve flap 38 of the specific exemplary embodiment.

The baseline vacuum valve 13 and the third opening 17 of the schematic illustration correspond to the sealing lip 311, the first and second backwash opening 45, 46 and the passage opening 32 in the valve body 3 of the specific exemplary embodiment.

The container valve 94 of the schematic illustration corresponds to the container valve of the specific exemplary embodiment.

The inlet 95 and the inlet valve 96 of the schematic illustration are formed in the above-described specific exemplary embodiment by the air-permeable and liquid-impermeable cover, i.e., by an appropriately chosen cover film.

These valves can also be implemented differently. Additionally, the valve openings can be housed in an additional module part, which is detachably connected to the breast shield. Moreover, the outlet opening 16 and/or the draining opening 19 can be embodied as a channel which extends in a line, in particular in a flexible line. Depending on the embodiment of this line, the pump chamber can be arranged at a distance from the breast shield and, depending on the embodiment, at a distance from a valve module, too. The valves can preferably be housed in a module which is arranged between the pump chamber and the breast shield funnel. If the pump chamber is arranged at a distance from the breast shield, the valve module can be arranged adjacent to the pump chamber or adjacent to the breast shield, or it can be a constituent part of the breast shield.

Figure 18:
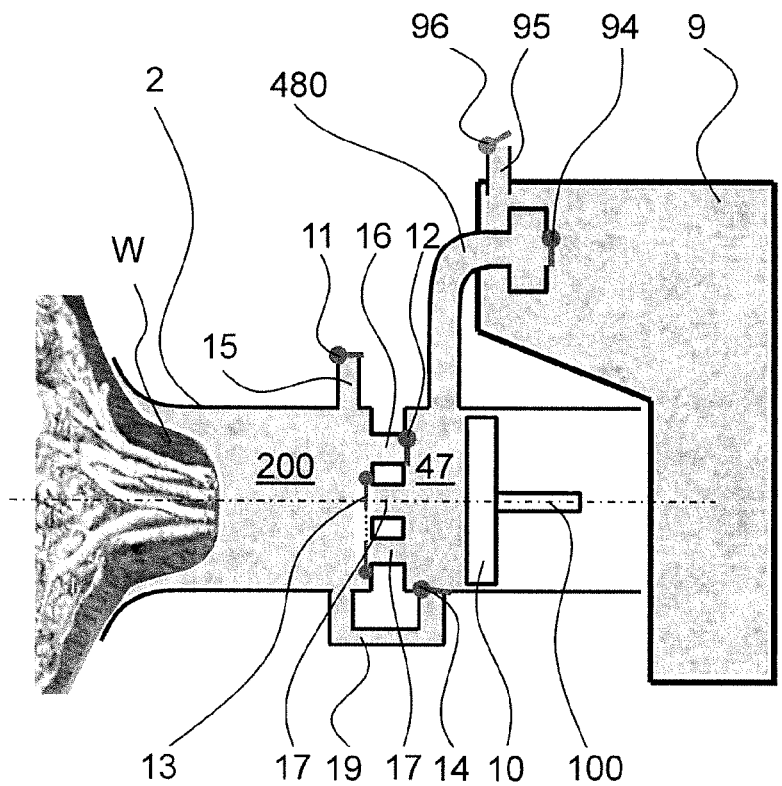
FIG. 18 shows a schematic illustration of the pump system according to the invention before the application of negative pressure.

The functionality is explained below:

The pump has not yet been activated in the illustration according to FIG. 18. Apart from the inlet valve 96 of the milk collection container 9, the valves are closed. Atmospheric pressure prevails in all regions, i.e., p=0.

Figure 19A:
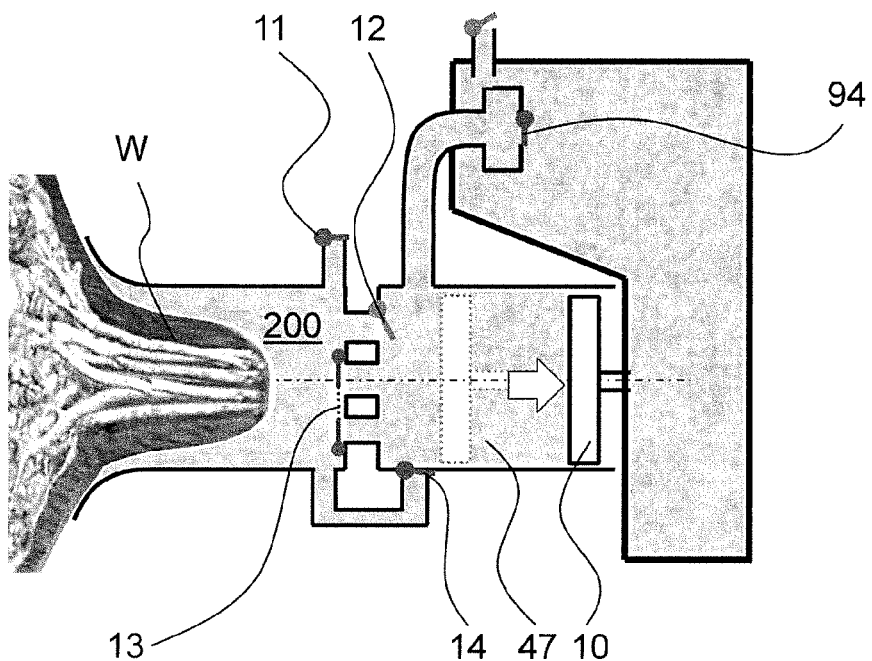
FIG. 19a shows the schematically illustrated pump system according to FIG. 1 during the activation of the mother's breast in a first stroke position.
Figure 19B:
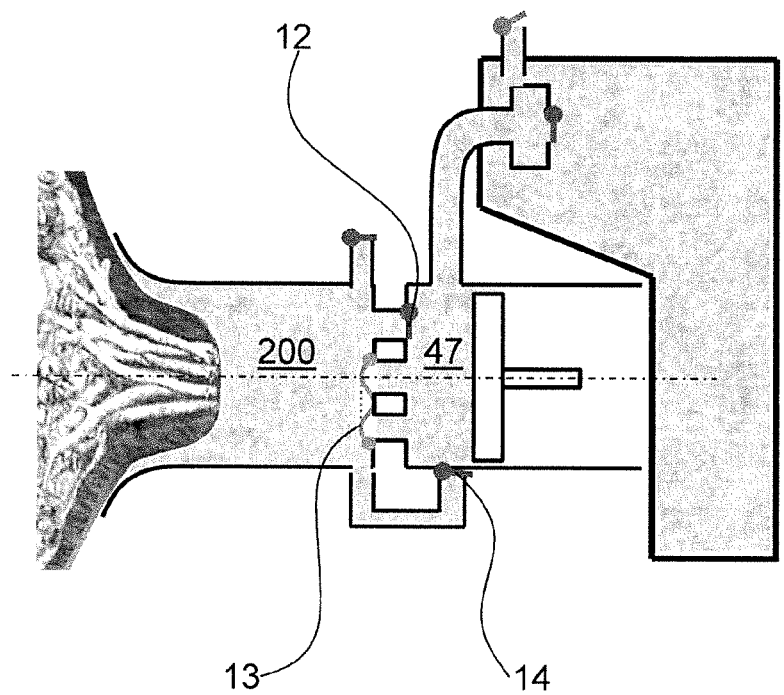
FIG. 19b shows the pump system according to FIG. 19a in a second stroke position.
Figure 19C:
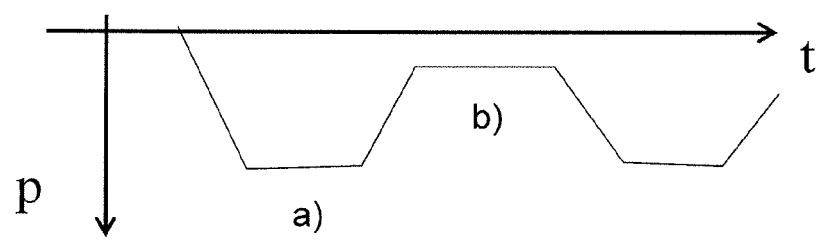
FIG. 19c shows a graphic illustration of the pressure within a breast shield when changing from the first stroke position to the second stroke position according to FIGS. 19a and 19b.

The pumping process starts in the illustration according to FIGS. 19a to 19c and the mother's breast is stimulated by the applied negative pressure. The pump valve 12 can open and close. To this end, the first outlet opening 24 and the first flow opening 25 are released and the first valve flap 37 opens and closes the valve in the specific exemplary embodiment. The draining valve 14 is securely closed. In the specific exemplary embodiment, this is implemented by virtue of the adjusting ring 5 being brought into the corresponding position and securely closing off the second outlet opening 27 and the second flow opening 28. The venting valve 11 likewise remains securely closed. In the specific exemplary embodiment, this is achieved by virtue of the first stud 34 closing off the first venting opening 26 by means of the adjusting ring 5.

The pump means 10, preferably a pump membrane or piston, is drawn to the outside in order to produce negative pressure in the pump chamber 47 (e.g. −150 mmHg in this case). The pump valve 12 opens and the negative pressure is transferred into the interior 200 of the breast shield 2 or air flows from this interior into the pump chamber 47. Consequently, negative pressure also prevails in the interior, ideally the same pressure of −150 mmHg, for example. The pressure profile in the interior 200 is illustrated in FIG. 19c. The pressure according to reference sign a) corresponds to the pressure in the interior 200 according to FIG. 19a. The container valve 94 remains closed. The pressure in the milk collection container 9 still is atmospheric pressure, i.e., p=0.

If the pump means 10 is now pushed back and the volume of the pump chamber 47 is reduced, the pump valve 12 closes and the pressure in the pump chamber 47 increases up to atmospheric pressure p=0. The pressure in the interior 200 likewise increases on account of the baseline vacuum valve 13 now being open. However, since the baseline vacuum valve 13 closes at a certain negative pressure, a baseline vacuum is maintained in the interior 200. By way of example, this lies at −20 mmHg. This situation is shown in FIG. 19b and the pressure profile in FIG. 19c is denoted by b).

By comparing FIGS. 19a and 19b, it is also possible to see how the nipple W stretches and retracts again in the interior 200.

Figure 20A:
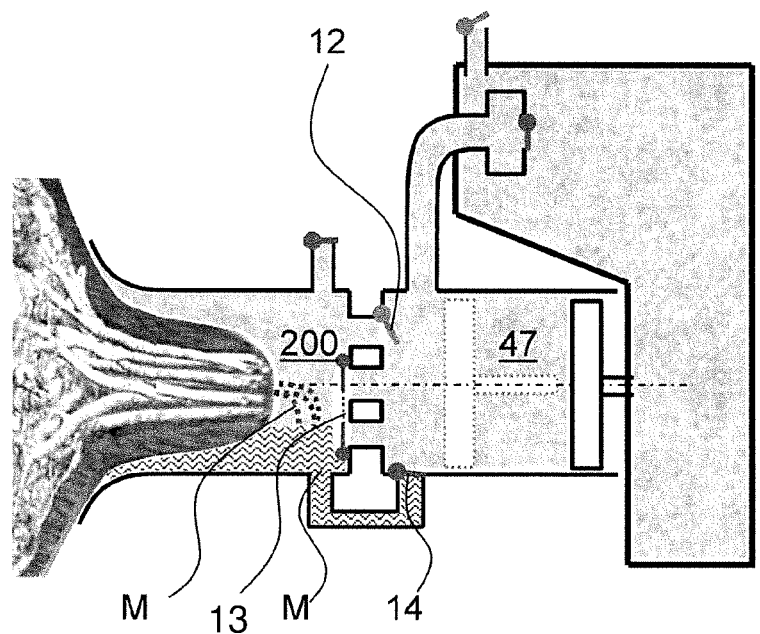
FIG. 20a shows the pump system according to FIG. 19a at the beginning of the milk flow from the breast in a first stroke position.
Figure 20B:
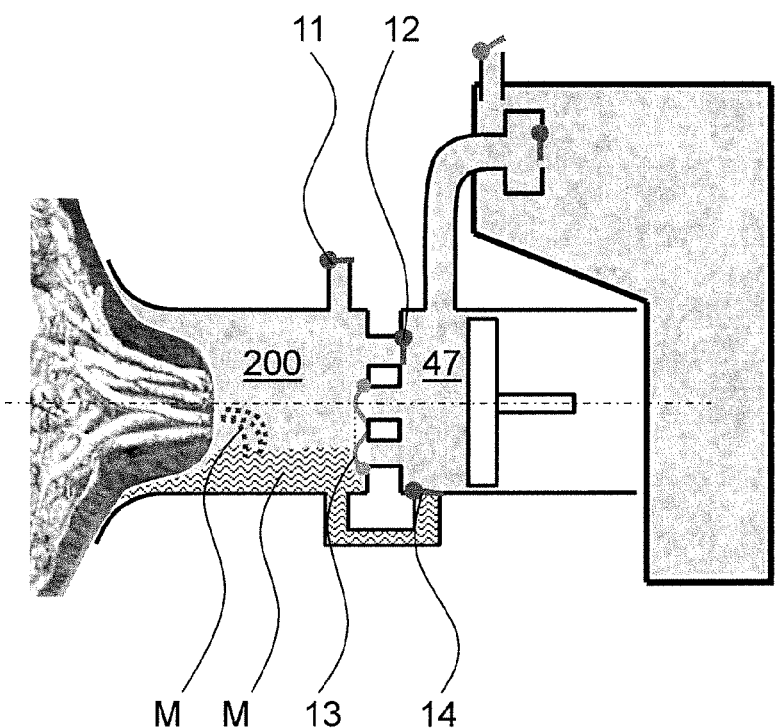
FIG. 20b shows the pump system according to FIG. 20a in a second stroke position.
Figure 20C:
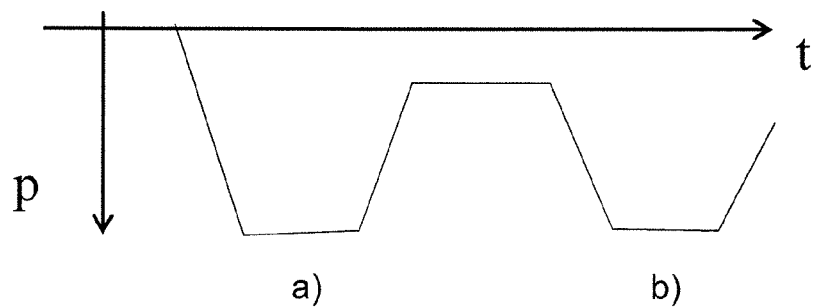
FIG. 20c shows a graphic illustration of the pressure within a breast shield when changing from the first stroke position to the second stroke position according to FIGS. 20a and 20b.

The milk flow from the mother's breast has started in FIGS. 20a to 20c. In the figures, the milk is denoted by the reference sign M. The interior 200 of the breast shield 2 fills with expressed milk. A milk lake arises below the pump valve 12. Thanks to the milk now present, the pump power increases with an unchanged drive power, for example to −170 mmHg in the pump chamber 47 and the interior 200. The pump valve 12 and the baseline vacuum valve 13 continue to open and close at each pump stroke, with the draining valve 14 and the venting valve 11 remaining closed. FIG. 20a shows the situation at maximum negative pressure (absolute value), which is also denoted by a) in FIG. 20c. FIG. 20b shows the situation when maintaining the baseline negative pressure in the interior 200 and atmospheric pressure in the pump chamber 47, which is denoted by b) in FIG. 20c.

As soon as the interior 200 is filled with milk M up to the outlet openings 16, milk M flows into the pump chamber 47 through the pump valve 12. The expressed milk M now also fills the pump chamber 47 until its fill level has reached the outlet opening 480 to the milk collection container 9. Now, the container valve 94 opens, preferably on account of the pressure of the collected milk M, and the milk M flows into the milk collection container 9.

Figure 21A:
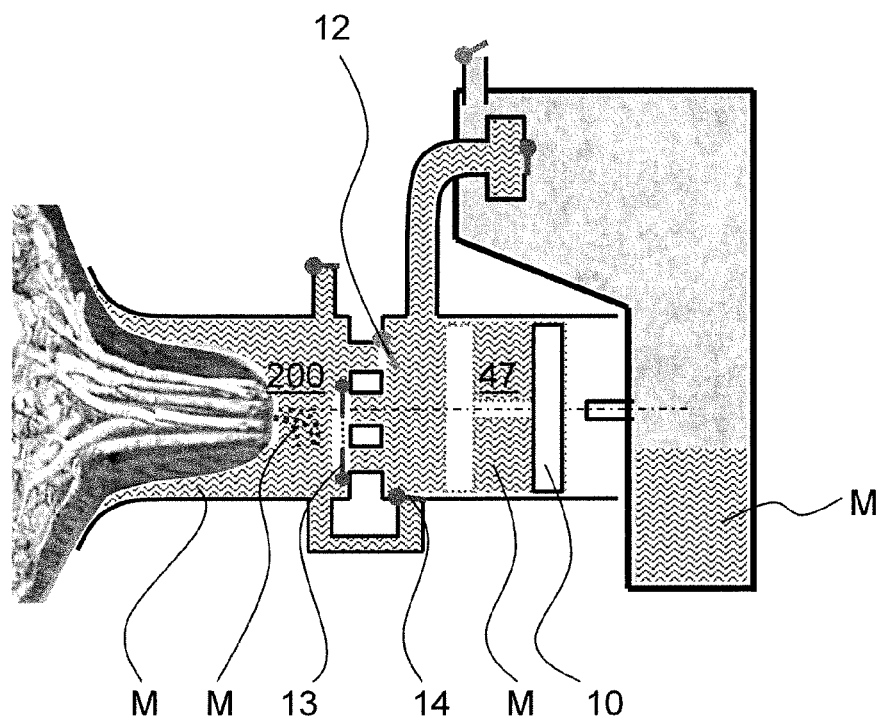
FIG. 21a shows the pump system according to FIG. 19a during the continuous milk flow from the breast in a first stroke position.
Figure 21B:
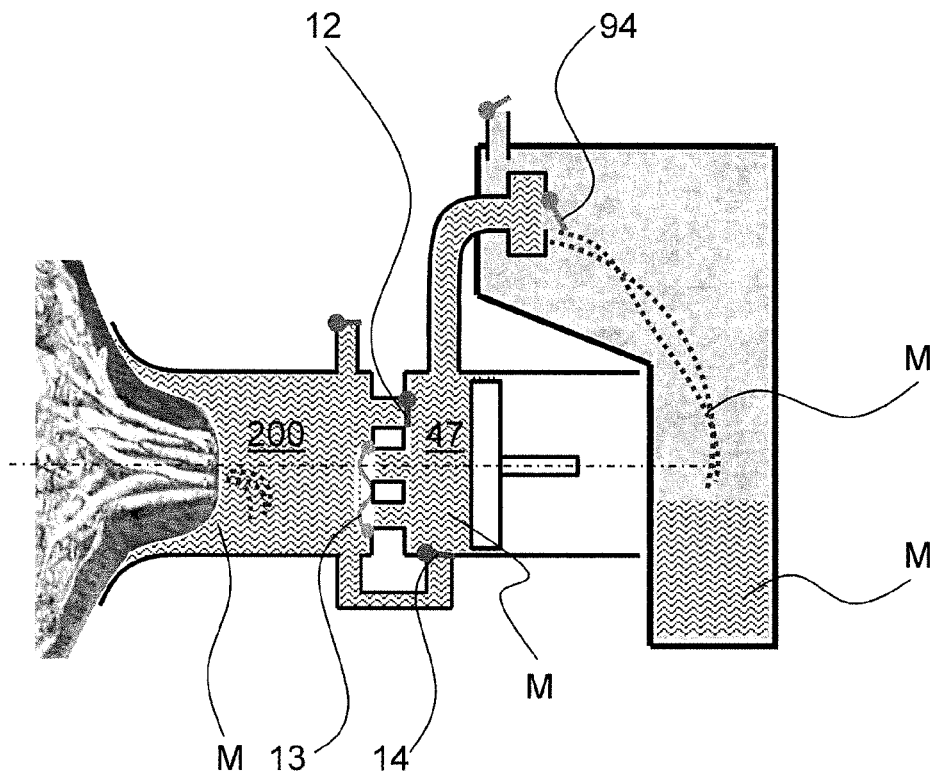
FIG. 21b shows the pump system according to FIG. 21a in a second stroke position.
Figure 21C:
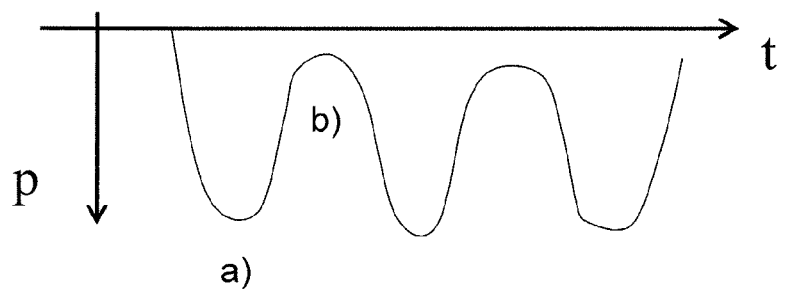
FIG. 21c shows a graphic illustration of the pressure within a breast shield when changing from the first stroke position to the second stroke position according to FIGS. 21a and 21b.

FIGS. 21a to 21c show the situation in which, ideally, no air is situated in the system anymore and the originally pneumatic system has completely changed into a hydraulic system. In practice, a mixed system is often present, wherein the expressed milk preferably fills a substantial part of the volumes and consequently forms the main working fluid.

As already explained on the basis of FIGS. 19a to 19c, the pump valve 12 and the baseline vacuum valve 13 open and close in accordance with the pump stroke, and so a negative pressure can be produced in the interior 200 and a baseline negative pressure can be maintained. Here, for example, the pressure in the pump chamber 47 alternates between −250 mmHg and 0 mmHg, the pressure in the interior alternates between −250 mmHg and −20 mmHg. The pressure in the milk collection container 9 remains at atmospheric pressure, i.e., at 0 mmHg. The pressure according to reference sign a) corresponds to the pressure in the interior 200 according to FIG. 21a and the pressure according to reference sign b) corresponds to the pressure in the interior 200 according to FIG. 21b.

Figure 22A:
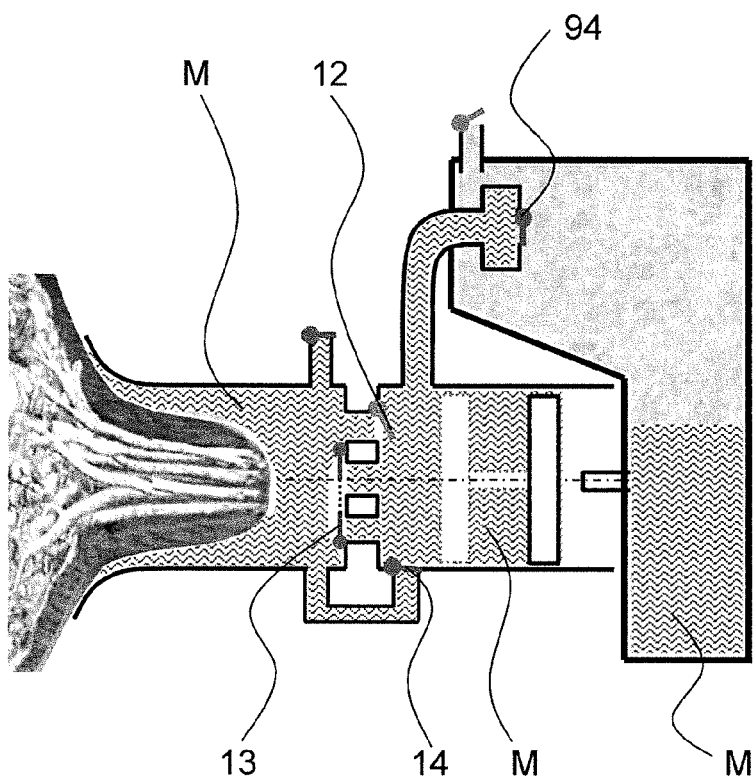
FIG. 22a shows the pump system according to FIG. 19a when terminating the milk flow in a first stroke position.
Figure 22B:
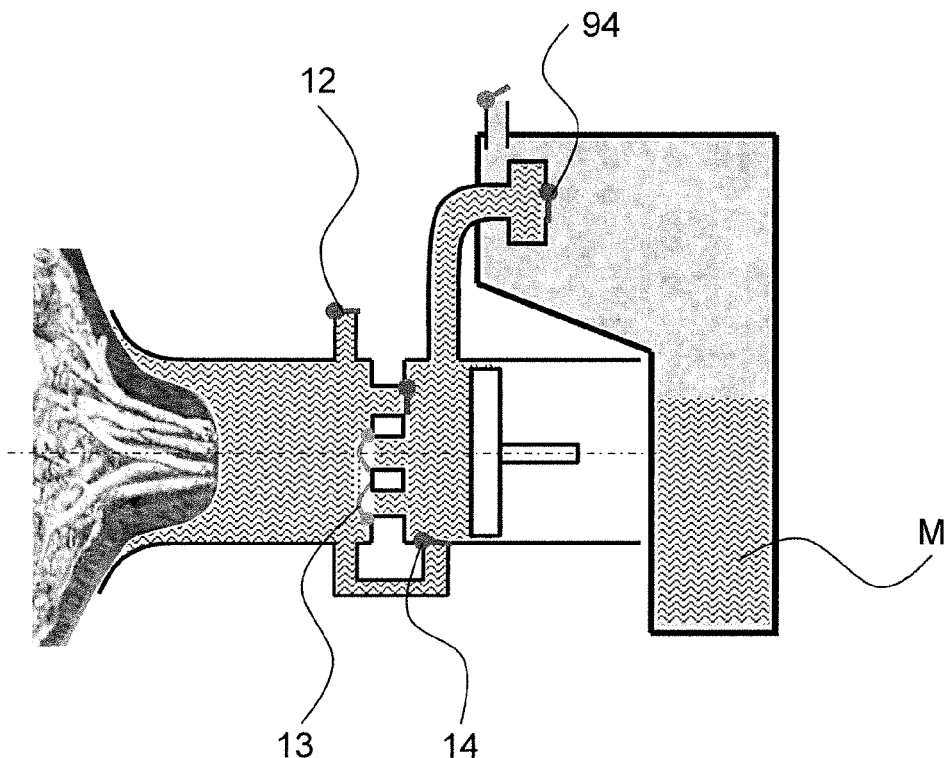
FIG. 22b shows the pump system according to FIG. 22a in a second stroke position.
Figure 22C:
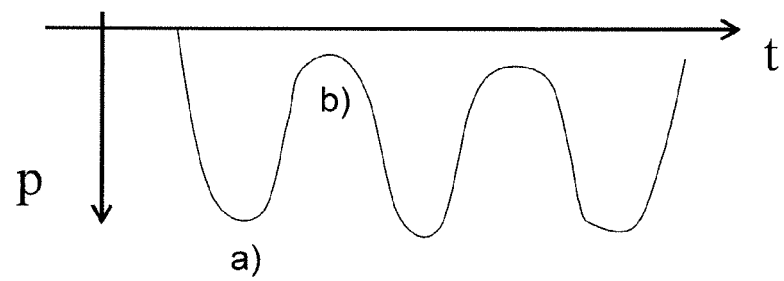
FIG. 22c shows a graphic illustration of the pressure within a breast shield when changing from the first stroke position to the second stroke position according to FIGS. 22a and 22b.

FIGS. 22a to 22c illustrate the situation in which no milk flows from the breast anymore. Initially, the system continues to pump, with the pump pressure no longer sufficing to open the container valve 94 to the milk collection container 9. This is the time at which the pump valve 12 is completely closed and, instead, the draining valve 14 is activated such that the latter can now be independently opened and closed. In the specific exemplary embodiment, the adjusting ring 5 is manually adjusted to this end. However, other types of activating and deactivating these two valves are possible. By way of example, they may be controlled by appropriate electronics. The pressure according to reference sign a) corresponds to the pressure in the interior 200 according to FIG. 22a and the pressure according to reference sign b) corresponds to the pressure in the interior 200 according to FIG. 22b.

Figure 23A:
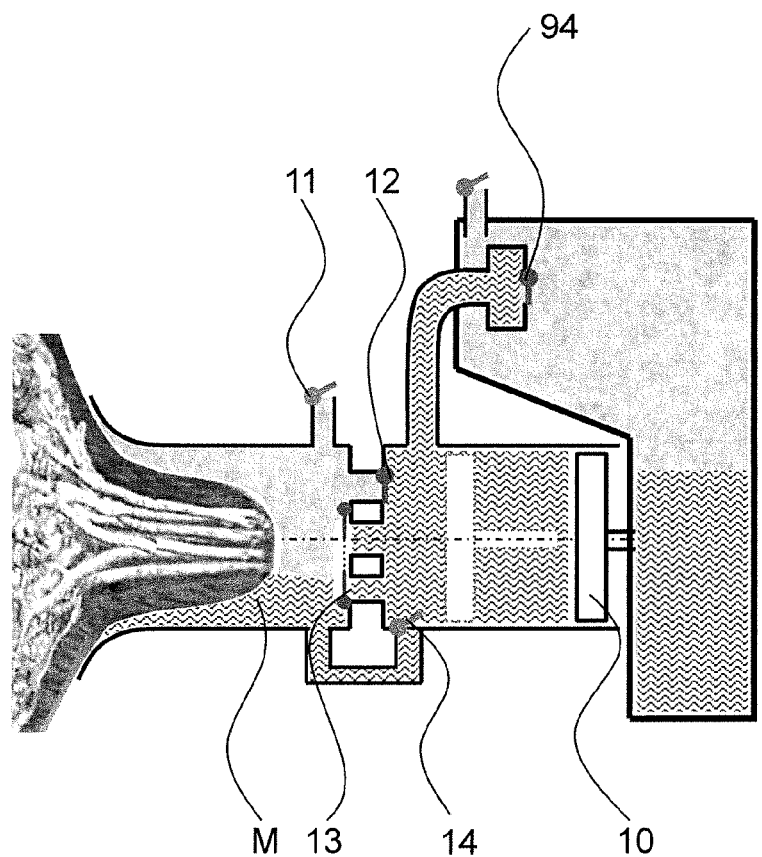
FIG. 23a shows the pump system according to FIG. 19a when draining in a first stroke position.
Figure 23B:
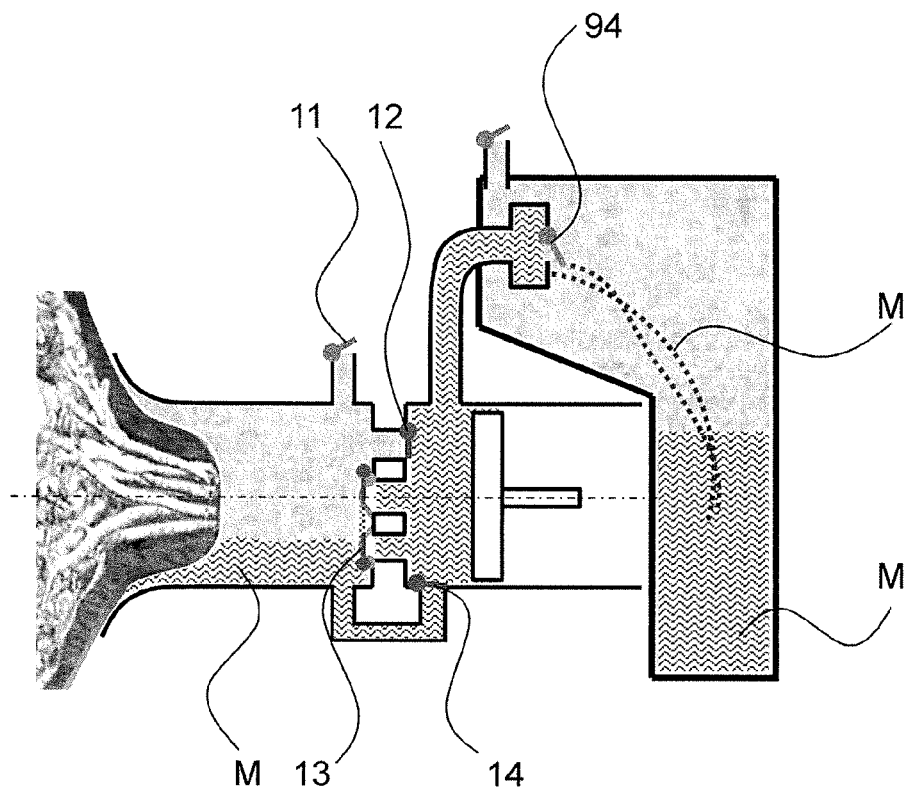
FIG. 23b shows the pump system according to FIG. 23a in a second stroke position and FIG. 23c shows a graphic illustration of the pressure within a breast shield when changing from the first stroke position to the second stroke position according to FIGS. 23a and 23b.
Figure 23C:
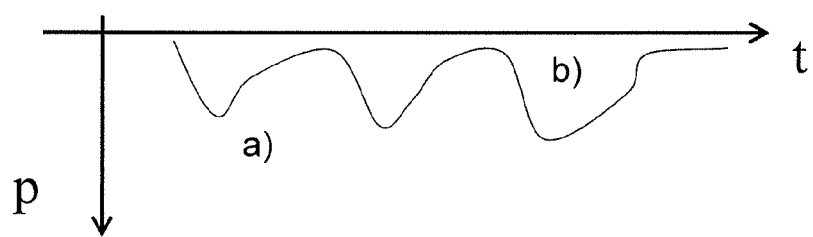

In the FIGS. 23a to 23c, the pump valve 12 is now securely closed off and the draining channel and the draining valve 14 are opened instead. The pump means 10 continues to move and continues to produce a pressure that alternates between a maximum negative pressure and atmospheric pressure in the pump chamber 47. As the pump valve 12 did previously, the draining valve 14 also opens and closes in accordance with this movement and consequently pumps the milk M from the interior 200 into the pump chamber 47. From there, it is conveyed into the milk collection container 9, preferably initially by means of negative pressure and subsequently by means of a displacement by the pump means 10. In this pump situation, the draining valve 14 is preferably situated in a lower position in the breast shield, preferably relatively far down. The lowering milk lake in the interior can easily be identified in FIGS. 23a and 23b. FIGS. 23a and 23b once again show the two extreme situations of a pump stroke. The pressure profile is illustrated in FIG. 23c. The pressure profile in the interior 200 is relatively nonspecific. The pressure according to reference sign a) corresponds to the pressure in the interior 200 according to FIG. 23a and the pressure according to reference sign b) corresponds to the pressure in the interior 200 according to FIG. 23b.

Consequently, the pump continues to be actuated during draining. Should milk still be in the pump chamber 47 at the end, it can easily be guided into the milk collection container 9 by tilting the pump or "placing it upside down".

Consequently, the breastpump according to the invention and the method according to the invention facilitate the use of expressed milk in a hydraulic pump system, as a result of which the drive of the pump can be minimized.

| | |
|---|---|
| 10 | Pump means |
| 100 | Spindle |
| 11 | Venting valve |
| 12 | Pump valve |
| 13 | Baseline vacuum valve |
| 14 | Draining valve |
| 15 | Venting opening |
| 16 | Outlet opening |
| 17 | Third opening |
| 19 | Draining opening |
| 2 | Breast shield |
| 20 | Funnel |
| 200 | Interior |
| 21 | Passage opening |
| 22 | Flange |
| 23 | Connector |
| 24 | First outlet opening |
| 25 | First flow opening |
| 26 | First venting opening |
| 27 | Second outlet opening |
| 28 | Second flow opening |
| 29 | Second venting opening |
| 3 | Valve body |
| 30 | Main body |
| 31 | Rear wall |
| 310 | Sealing area |
| 311 | Sealing lip |
| 312 | Furrow |
| 32 | Passage opening |
| 33 | Positioning lug |
| 34 | First stud |
| 35 | Venting stud |
| 36 | Second stud |
| 37 | First valve flap |
| 38 | Second valve flap |
| 4 | Adapter part |
| 40 | Main body |
| 400 | First window |
| 401 | Second window |
| 402 | Positioning aid |
| 41 | Pump-side wall |
| 410 | Channel wall |
| 42 | Elevated wall part |
| 43 | First passage opening |
| 44 | Second passage opening |
| 45 | First backwash opening |
| 46 | Second backwash opening |
| 47 | Pump chamber |
| 48 | Groove |
| 480 | Outlet opening |
| 49 | Outlet |
| 5 | Adjusting ring |
| 50 | First part |
| 51 | First connector part |
| 52 | Second part |
| 53 | Second connector part |
| 54 | Latching element |
| 55 | Stop |
| 56 | First pressure element |
| 57 | Second pressure element |
| 58 | Actuation lever |
| 6 | Media separation membrane |
| 60 | Membrane area |
| 61 | Central region |
| 62 | Sealing area |
| 63 | Groove |
| 64 | Recess |
| 7 | Pump membrane |
| 70 | Membrane area |
| 71 | Central region |
| 72 | Passage opening |
| 73 | Reinforcement |
| 74 | Sealing area |
| 75 | Sensor area |
| 76 | Vane |
| 77 | Side wings |
| 8 | Pump housing |
| 8' | Carrier module |
| 80 | Side arm |
| 81 | Motor receptacle |
| 82 | Spindle receptacle |

-continued

| | |
|---|---|
| 83 | Spindle |
| 84 | Fastening holes |
| 85 | Edge |
| 86 | Actuation switch |
| 87 | Display |
| 9 | Milk collection container |
| 90 | Vessel |
| 900 | Interior |
| 901 | First latching element |
| 902 | Second latching element |
| 91 | Lower frame part |
| 92 | Cover |
| 93 | Upper frame part |
| 930 | Frame |
| 931 | Braces |
| 932 | Valve receptacle |
| 933 | Handle |
| 934 | Spacer pins |
| 94 | Container valve |
| 95 | Inlet |
| 96 | Inlet valve |
| W | Nipple |
| M | Milk |

The invention claimed is:

1. A breastpump for expressing human breastmilk, wherein the breastpump comprises a housing with a drive unit, a pump chamber with a flexible pump membrane, driven by the drive unit, for producing a vacuum, and a breast shield with an interior for receiving the expressed breastmilk,
    wherein a cyclically changing negative pressure is applicable to the interior by means of the pump chamber,
    wherein a milk channel leads from the interior into the pump chamber through a first inlet opening, wherein the expressed breastmilk flows from the interior of the breast shield into the pump chamber through the milk channel and wherein the pump chamber has an outlet opening, through which the expressed breastmilk flows from the pump chamber into a milk collection container,
    a multipart hygiene module comprising a first part with a flow opening for connecting to the interior, a valve body with at least one valve, and a second part with a rigid cup for forming the pump chamber, wherein the breast shield is directly connected to the housing of the breastpump in a detachable manner, and the valve body is arranged between and sealingly engages the first part and the second part when the breast shield is connected to the housing of the breastpump.

2. The breastpump as claimed in claim 1, the rigid cup having a milk path which leads from the pump chamber into the milk collection container and which, at least over a portion, extends perpendicular to a drive axis of the pump membrane.

3. The breastpump as claimed in claim 1, wherein the at least one valve of the valve body comprises at least one flow valve and one venting valve.

4. The breastpump as claimed in claim 1, wherein the valve body is formed in integral fashion from a flexible material.

5. The breastpump as claimed in claim 1, wherein the first part is a constituent part of the breast shield.

6. The breastpump as claimed in claim 1, the breast shield having a flange for detachably connecting to the housing.

7. The breastpump as claimed in claim 6, wherein the detachable connection between the flange of the breast shield and the housing is an interlocking and a force fit.

8. The breastpump as claimed in claim 6, wherein the detachable connection between the flange of the breast shield and the housing is a bayonet lock.

9. The breastpump as claimed in claim 1, wherein the breast shield has a first passage opening, which forms part of the milk channel, wherein the first passage opening, at least at a start of an expressing process, is arranged in an upper region of the interior in a use position of the breast shield such that the interior below the first passage opening is fillable with the expressed breastmilk.

10. The breastpump as claimed in claim 1, wherein the milk channel is able to be closed off by means of a first valve of the at least one valve of the valve body in order to remove the expressed breastmilk from the pump chamber at an end of an expressing process.

11. The breastpump as claimed in claim 1, wherein a draining channel is present between the interior of the breast shield and the pump chamber, said draining channel extending separately from the milk channel, and wherein the draining channel is able to be closed off by means of a second valve of the at least one valve of the valve body, wherein the draining channel is closed during an expressing process and opened at an end of the expressing process.

12. The breastpump as claimed in claim 11, wherein the at least one valve of the valve body comprises a venting valve for venting the interior of the breast shield and wherein the venting valve is able to be closed off together with the second valve of the at least one valve of the valve body and said venting valve can be opened together with the latter.

13. The breastpump as claimed in claim 1, wherein the at least one valve of the valve body comprises a venting valve for venting the interior of the breast shield.

14. The breastpump as claimed in claim 1, wherein the at least one valve of the valve body comprises a third valve, said third valve maintaining a baseline negative pressure in the interior of the breast shield when the cyclically changing negative pressure increases.

15. The breastpump as claimed in claim 1, wherein the at least one valve of the valve body comprises a fourth valve in the milk channel, said fourth valve opening and closing in accordance with the applied cyclically changing negative pressure.

16. The breastpump as claimed in claim 1, wherein the at least one valve of the valve body comprises a fifth valve in a draining channel, said fifth valve opening and closing in accordance with the applied cyclically changing negative pressure.

17. The breastpump as claimed in claim 1, wherein the at least one valve of the valve body comprises at least two valves and wherein the at least two valves are arranged in the valve body.

18. The breastpump as claimed in claim 17, wherein the valve body is integral and flexible.

19. The breastpump as claimed in claim 18, wherein; the rigid cup is a constituent part of the multipart hygiene module, which is connectable together to the housing; the multipart hygiene module comprises the at least two valves; the rigid cup is a constituent part of an adapter part; and the valve body is held in a receptacle of the adapter part.

20. The breastpump as claimed in claim 19, wherein the multipart hygiene module further comprises a manual actuation means for simultaneous actuation of the at least two valves.

21. The breastpump as claimed in claim 20, wherein the adapter part and the manual actuation means are not detachable from one another in a non-destructive manner.

22. A breastpump for expressing human breastmilk, wherein the breastpump comprises a breast shield with an interior for receiving a mother's breast and a pump chamber comprising a first cup and a flexible pump membrane, wherein the pump membrane rests against the first cup in sealing fashion and the pump membrane is driven and a cyclically changing negative pressure is producible in the pump chamber as a result of movement of said pump membrane relative to the first cup, wherein the cyclically changing negative pressure is appliable to the interior by means of the pump chamber, wherein a milk channel leads from the interior into the pump chamber through a first inlet opening, the expressed breastmilk flowing through said milk channel from the interior of the breast shield into the pump chamber, wherein the pump chamber has an outlet opening, through which the expressed breastmilk flows from the pump chamber into a milk collection container, wherein the outlet opening, at least at a start of an expressing process, is arranged in an upper region of the pump chamber and/or above the first inlet opening in a vertical use position of the breastpump, and wherein the first cup has an outlet groove that extends from the outlet opening of the pump chamber to an output, the outlet groove, at least over a portion, extending in a direction of fluid flow perpendicular to a movement direction of the pump membrane and the pump membrane closes off the outlet groove of the first cup to form a channel for fluid flow between the outlet opening and the output.

23. The breastpump as claimed in claim 22, wherein the milk channel forms a vacuum channel for applying the cyclically changing negative pressure to the interior of the breast shield.

24. The breastpump as claimed in claim 22, wherein a flexible media separation membrane is arranged between the first cup and the flexible pump membrane such that the pump membrane is protected from contact with the expressed breastmilk.

25. The breastpump as claimed in claim 24, wherein the media separation membrane closes off the outlet groove of the first cup to form a channel that is closed apart from the outlet opening and the output.

26. The breastpump as claimed in claim 22, wherein the breastpump comprises a pump housing with a drive unit for the pump membrane and wherein the first cup is detachably connected to the pump housing.

27. The breastpump as claimed in claim 26, wherein the first cup is a constituent part of the multipart hygiene module, which is connectable together to the pump housing, wherein the multipart hygiene module further comprises at least two valves.

28. The breastpump as claimed in claim 27, wherein; the breast shield is fastenable to the pump housing in a detachable manner; as a result of fastening the breast shield to the pump housing, the first cup and the flexible pump membrane are connected to one another in sealing fashion such that a tight connection arises between the pump chamber and the interior of the breast shield; and the breast shield and the at least two valves are parts of the multipart hygiene module.

29. The breastpump as claimed in claim 22, wherein: the breastpump comprises a pump housing; the breast shield is fastenable to the pump housing in a detachable manner; and as a result of fastening the breast shield to the pump housing, the first cup and the flexible pump membrane are connected to one another in sealing fashion such that a tight connection arises between the pump chamber and the interior of the breast shield.

30. The breastpump as claimed in claim 22, wherein the breastpump comprises a pump housing, to which the breast shield is fastenable in a detachable manner, and wherein the breastpump further comprises the milk collection container, which is fastenable to the pump housing by means of a snap-fit connector.

31. The breastpump as claimed in claim 30, wherein the milk collection container comprises a main body and a lid, wherein the lid is at least partly air-permeable and liquid-impermeable.

32. The breastpump as claimed in claim 31, wherein the lid comprises an air-permeable and liquid-impermeable membrane.

33. The breastpump as claimed in claim 31, wherein the lid is provided with a one-way valve.

34. A method for actuating a breastpump for expressing human breastmilk, wherein the breastpump comprises a breast shield with an interior for receiving a mother's breast and a pump chamber, wherein a cyclically changing negative pressure is applied to the interior by means of the pump chamber,
wherein, in a first pump phase, the cyclically changing negative pressure is applied to the interior via a pump valve and a baseline vacuum valve in order to express the breastmilk from the mother's breast, wherein the interior is filled with the expressed breastmilk without the expressed breastmilk flowing out of the interior,
wherein, in a second pump phase, the expressed breastmilk flows from the interior into the pump chamber through the pump valve and the pump chamber is filled with the expressed breastmilk,
wherein, in a third pump phase, the expressed breastmilk flows from the pump chamber into a milk collection container, with the interior and the pump chamber remaining filled with the expressed breastmilk, and
wherein a change from the second pump phase to the third pump phase is implemented by virtue of a fill level of the expressed breastmilk reaching an outlet opening, which leads from the pump chamber to the milk collection container, as a result of which the expressed breastmilk flows from the pump chamber into the milk collection container through the outlet opening.

35. The method as claimed in claim 34, wherein the breastpump changes from a pneumatic pump system to a hydraulic pump system during an expressing process, wherein the first pump phase is a pneumatic pump phase and the second pump phase is a hydraulic pump phase.

36. The method as claimed in claim 34, wherein the interior is nearly completely filled during the first pump phase.

37. The method as claimed in claim 34, wherein at least one of the interior or the pump chamber are nearly completely filled with the expressed breastmilk during at least one of the second or third pump phase.

38. The method as claimed in claim 34, wherein a change from the first pump phase to the second pump phase is implemented by virtue of a fill level of the expressed breastmilk reaching a first passage opening, which leads from the interior to the pump chamber, as a result of which the expressed breastmilk flows from the interior into the pump chamber through the first passage opening.

39. The method as claimed in claim 38, wherein, in the third pump phase, the expressed breastmilk flows through the first passage opening into the pump chamber and flows through the outlet opening into the milk collection container.

40. The method as claimed in claim 34, wherein a baseline negative pressure is maintained during at least some of the pump phases.

41. The method as claimed in claim 40, wherein the baseline vacuum valve initially opens in the case of a pressure increase of the cyclically changing negative pressure in a direction of atmospheric pressure and then closes, thereby maintaining the baseline negative pressure.

42. The method as claimed in claim 40, wherein the baseline negative pressure is maintained during at least the first, second, and third pump phase.

43. A method for actuating a breastpump for expressing human breastmilk, wherein the breastpump comprises a breast shield with an interior for receiving a mother's breast and a pump chamber, wherein a cyclically changing negative pressure is applied to the interior by means of the pump chamber,
wherein, in a first pump phase, the cyclically changing negative pressure is applied to the interior in order to express the breastmilk from the mother's breast, wherein the interior is filled with the expressed breastmilk without the expressed breastmilk flowing out of the interior,
wherein, in a second pump phase, the expressed breastmilk flows from the interior into the pump chamber and the pump chamber is filled with the expressed breastmilk,
wherein, in a third pump phase, the expressed breastmilk flows from the pump chamber into a milk collection container, with the interior and the pump chamber remaining filled with the expressed breastmilk,
wherein a change from the first pump phase to the second pump phase is implemented by virtue of a fill level of the expressed breastmilk reaching a first passage opening, which leads from the interior to the pump chamber, as a result of which the expressed breastmilk flows from the interior into the pump chamber through the first passage opening,
wherein a change from the second pump phase to the third pump phase is implemented by virtue of a fill level of the expressed breastmilk reaching an outlet opening, which leads from the pump chamber to the milk collection container, as a result of which the expressed breastmilk flows from the pump chamber into the milk collection container through the outlet opening, and
wherein, in a fourth pump phase, the interior is drained and the expressed breastmilk contained therein is guided from the interior to the milk collection container through a second passage opening.

44. The method as claimed in claim 43, wherein the first passage opening is able to be closed off with a first valve and wherein the second passage opening is able to be closed off with a second valve, wherein the second passage opening always remains closed during the first to third pump phases and wherein, in a fourth pump phase, the interior is drained and the expressed breastmilk contained therein is guided from the interior to the milk collection container through the second passage opening.

45. The method as claimed in claim 44, wherein the first passage opening is always closed during the fourth pump phase.

46. The method as claimed in claim 45, wherein the second passage opening leads from the interior into the pump chamber and has a fluid-communicating connection to the outlet opening via the pump chamber.

* * * * *